United States Patent
Knox et al.

(10) Patent No.: US 9,645,081 B2
(45) Date of Patent: May 9, 2017

(54) PARTICLE DETECTION

(71) Applicant: Xtralis Technologies Ltd, Nassau (BS)

(72) Inventors: Ron Knox, Mount Eliza (AU); Kate Cooper, Caufield North (AU); Kemal Ajay, Mount Waverley (AU)

(73) Assignee: Xtralis Technologies Ltd, Nassau (BS)

(*) Notice: Subject to any disclaimer, the term of this patent is extended or adjusted under 35 U.S.C. 154(b) by 0 days.

(21) Appl. No.: 14/954,141

(22) Filed: Nov. 30, 2015

(65) Prior Publication Data

US 2016/0077001 A1 Mar. 17, 2016

Related U.S. Application Data

(63) Continuation of application No. 14/318,033, filed on Jun. 27, 2014, now Pat. No. 9,267,884, which is a (Continued)

(30) Foreign Application Priority Data

Jun. 10, 2008 (AU) ................................ 2008902909
Jun. 26, 2008 (AU) ................................ 2008903268
(Continued)

(51) Int. Cl.
*G01N 21/00* (2006.01)
*G01N 21/53* (2006.01)
(Continued)

(52) U.S. Cl.
CPC .......... *G01N 21/53* (2013.01); *G01N 15/0205* (2013.01); *G01N 15/0227* (2013.01);
(Continued)

(58) Field of Classification Search
CPC .......... G02B 2027/0178; G02B 27/017; G02B 2027/014; G02B 27/0093;
(Continued)

(56) References Cited

U.S. PATENT DOCUMENTS

| 3,504,566 A | 4/1970 | Zurcher |
|---|---|---|
| 3,982,130 A | 9/1976 | Trumble |

(Continued)

FOREIGN PATENT DOCUMENTS

| EP | 1300816 A1 | 4/2003 |
|---|---|---|
| GB | 2319604 A | 5/1998 |

(Continued)

OTHER PUBLICATIONS

"U.S. Appl. No. 12/997,155, Non Final Office Action mailed Oct. 29, 2013", 10 pgs.

(Continued)

*Primary Examiner* — Michael P Stafira

(74) *Attorney, Agent, or Firm* — Schwegman Lundberg & Woessner, P.A.

(57) ABSTRACT

A particle detection system including; at least one light source adapted to illuminate a volume being monitored at at least two wavelengths; a receiver having a field of view and being adapted to receive light from at least one light source after said light has traversed the volume being monitored and being adapted to generate signals indicative of the intensity of light received at regions within the field of view of the receiver; a processor associated with the receiver adapted to process the signals generated by the receiver to correlate light received at at least two wavelengths in corresponding regions within the field of view of the receiver and generate an output indicative of the relative level of light received at the two wavelengths.

12 Claims, 24 Drawing Sheets

Related U.S. Application Data continuation of application No. 12/997,155, filed as application No. PCT/AU2009/000727 on Jun. 10, 2009, now Pat. No. 8,804,119.

(30) Foreign Application Priority Data

| Jun. 26, 2008 | (AU) | ................................ 2008903269 |
|---|---|---|
| Jun. 26, 2008 | (AU) | ................................ 2008903270 |
| May 1, 2009 | (AU) | ................................ 2009901923 |

(51) Int. Cl.

| G08B 17/107 | (2006.01) |
|---|---|
| G01N 15/02 | (2006.01) |
| G01N 21/49 | (2006.01) |
| G08B 17/113 | (2006.01) |

(52) U.S. Cl.
CPC ........... *G01N 21/49* (2013.01); *G01N 21/538* (2013.01); *G08B 17/107* (2013.01); *G01N 2201/0621* (2013.01); *G01N 2201/0696* (2013.01); *G08B 17/113* (2013.01)

(58) Field of Classification Search
CPC .... G02B 2027/0118; G02B 2027/0187; G02B 27/0172; G02B 2027/0138; G02B 27/0176; G02B 5/30; G02B 2027/0127; G02B 2027/0132; G02B 2027/01

See application file for complete search history.

(56) References Cited

U.S. PATENT DOCUMENTS

| 4,156,816 | A | * | 5/1979 | Lindgren ............. G08B 17/103 250/574 |
|---|---|---|---|---|
| 4,163,969 | A | | 8/1979 | Enemark |
| 4,348,111 | A | | 9/1982 | Goulas et al. |
| 4,387,993 | A | | 6/1983 | Adrian |
| 4,547,675 | A | | 10/1985 | Muggli et al. |
| 4,854,705 | A | | 8/1989 | Bachalo |
| 4,857,895 | A | | 8/1989 | Kaprelian |
| 4,927,268 | A | | 5/1990 | Carr |
| 4,928,153 | A | | 5/1990 | Glass |
| 5,189,631 | A | | 2/1993 | Suzuki |
| 5,260,765 | A | | 11/1993 | Hawkinson |
| 5,392,114 | A | | 2/1995 | Cole |
| 5,451,931 | A | | 9/1995 | Muller et al. |
| 5,694,221 | A | | 12/1997 | Knapp |
| 6,011,478 | A | | 1/2000 | Suzuki et al. |
| 6,266,137 | B1 | | 7/2001 | Morinaga |
| 7,250,871 | B2 | | 7/2007 | Williams et al. |
| 7,292,338 | B2 | | 11/2007 | Itagaki |
| 7,525,660 | B2 | | 4/2009 | Gigioli et al. |
| 7,564,365 | B2 | | 7/2009 | Marman et al. |
| 7,671,988 | B2 | | 3/2010 | Dal Sasso et al. |
| 8,098,362 | B2 | | 1/2012 | Kanaya |
| 8,339,598 | B2 | | 12/2012 | Ban et al. |
| 8,508,376 | B2 | | 8/2013 | Knox et al. |
| 8,620,031 | B2 | | 12/2013 | Knox et al. |
| 8,797,531 | B2 | | 8/2014 | Knox et al. |
| 8,804,119 | B2 | | 8/2014 | Knox et al. |
| 9,057,485 | B2 | | 6/2015 | Knox et al. |
| 9,267,884 | B2 | | 2/2016 | Knox et al. |
| 9,448,168 | B2 | | 9/2016 | Knox et al. |
| 2001/0039680 | A1 | | 11/2001 | Boucher et al. |
| 2002/0153499 | A1 | | 10/2002 | Oppelt et al. |
| 2003/0189487 | A1 | | 10/2003 | Mathews et al. |
| 2004/0075056 | A1 | | 4/2004 | Bell et al. |
| 2005/0069207 | A1 | | 3/2005 | Zakrzewski et al. |
| 2005/0178194 | A1 | | 8/2005 | Barker-mill |
| 2005/0259255 | A1 | | 11/2005 | Williams et al. |
| 2006/0065860 | A1 | | 3/2006 | Jones |
| 2006/0202847 | A1 | | 9/2006 | Oppelt et al. |
| 2006/0232773 | A1 | | 10/2006 | Barton et al. |
| 2006/0261967 | A1 | | 11/2006 | Marman et al. |
| 2006/0269277 | A1 | | 11/2006 | Speggiorin |
| 2007/0040694 | A1 | | 2/2007 | Williams et al. |
| 2007/0064980 | A1 | * | 3/2007 | Knox .................... G01N 21/53 382/128 |
| 2007/0097372 | A1 | | 5/2007 | Itagaki |
| 2008/0021674 | A1 | | 1/2008 | Puskas |
| 2008/0069575 | A1 | | 3/2008 | Harada |
| 2008/0144169 | A1 | | 6/2008 | Zahniser et al. |
| 2008/0198027 | A1 | | 8/2008 | Bugge |
| 2008/0297360 | A1 | * | 12/2008 | Knox .................... G01N 21/49 340/628 |
| 2008/0316039 | A1 | | 12/2008 | White et al. |
| 2009/0004580 | A1 | | 1/2009 | Kanaya |
| 2009/0109043 | A1 | | 4/2009 | Luterotti |
| 2011/0221889 | A1 | | 9/2011 | Knox et al. |
| 2012/0140231 | A1 | | 6/2012 | Knox et al. |
| 2014/0306113 | A1 | * | 10/2014 | Knox .................... G01N 21/53 250/338.5 |
| 2014/0340892 | A1 | | 11/2014 | Knox et al. |
| 2015/0276593 | A1 | | 10/2015 | Knox et al. |

FOREIGN PATENT DOCUMENTS

| GB | 2426323 A | 11/2006 |
|---|---|---|
| GB | 2450132 A | 12/2008 |
| JP | S51127786 | 11/1976 |
| JP | 54-008578 A | 1/1979 |
| JP | S55080037 A | 6/1980 |
| JP | 56-132692 U | 10/1981 |
| JP | H01121737 | 5/1989 |
| JP | 03-188596 A | 8/1991 |
| JP | 3-239949 A | 10/1991 |
| JP | 04-024797 A | 1/1992 |
| JP | H04059454 U | 5/1992 |
| JP | H06034540 A | 2/1994 |
| JP | 06109631 | 4/1994 |
| JP | H06109631 | 4/1994 |
| JP | H11295233 | 10/1999 |
| JP | H11304582 | 11/1999 |
| JP | 11-339156 A | 12/1999 |
| JP | 2000-019112 A | 1/2000 |
| JP | 2001-116692 | 4/2001 |
| JP | 2001-331878 | 11/2001 |
| JP | 2003-281643 | 10/2003 |
| JP | 2004-104727 | 4/2004 |
| JP | 2004-325211 | 11/2004 |
| JP | 2005-504300 | 2/2005 |
| JP | 2005-115970 | 4/2005 |
| JP | 2007-057360 | 3/2007 |
| JP | 2007-507705 A | 3/2007 |
| JP | 2007-179266 | 7/2007 |
| JP | 2007-533966 | 11/2007 |
| JP | 2007-533971 | 11/2007 |
| JP | 2008-519965 A | 6/2008 |
| TW | 200915010 | 4/2009 |
| WO | WO-01/59737 A1 | 8/2001 |
| WO | WO-2004/102498 A1 | 11/2004 |
| WO | WO-2006/050570 A1 | 5/2006 |
| WO | WO-2006/091328 A2 | 8/2006 |
| WO | WO-2008/064396 A1 | 6/2008 |
| WO | WO-2009/062256 A9 | 5/2009 |
| WO | WO-2009/149498 A1 | 12/2009 |
| WO | WO-2010/124347 A1 | 11/2010 |

OTHER PUBLICATIONS

"U.S. Appl. No. 12/997,155, Notice of Allowance mailed Mar. 28, 2014", 12 pgs.

"U.S. Appl. No. 12/997,155, Response filed Jan. 22, 2014 to Non Final Office Action mailed Oct. 29, 2013", 11 pgs.

"U.S. Appl. No. 13/318,309, Non Final Office Action mailed Sep. 26, 2013", 8 pgs.

"U.S. Appl. No. 13/318,309, Notice of Allowance mailed Mar. 31, 2014", 11 pgs.

"U.S. Appl. No. 13/318,309, PTO Response to Rule 312 Communication mailed Jun. 2, 2014", 2 pgs.

(56) References Cited

OTHER PUBLICATIONS

"U.S. Appl. No. 13/318,309, Response filed Jan. 22, 2014 to Non Final Office Action mailed Sep. 26, 2013", 15 pgs.
"U.S. Appl. No. 13/318,309, Response filed Aug. 20, 2013 to Restriction Requirement mailed Jul. 8, 2013", 10 pgs.
"U.S. Appl. No. 13/318,309, Restriction Requirement mailed Jul. 8, 2013", 6 pgs.
"U.S. Appl. No. 14/318,033, Non Final Office Action mailed Mar. 5, 2015", 6 pgs.
"U.S. Appl. No. 14/318,033, Notice of Allowance mailed Sep. 29, 2015", 8 pgs.
"U.S. Appl. No. 14/318,033, Preliminary Amendment filed Jul. 22, 2014", 4 pgs.
"U.S. Appl. No. 14/318,033, Response filed Aug. 5, 2015 to Non Final Office Action mailed Mar. 5, 2015", 8 pgs.
"U.S. Appl. No. 14/451,330, Notice of Allowance mailed Feb. 25, 2015", 10 pgs.
"U.S. Appl. No. 14/738,371, Non Final Office Action mailed Jul. 16, 2015", 8 pgs.
"Chinese Application Serial No. 200980130131.9, Office Action mailed Jul. 8, 2014", (English Translation), 14 pgs.
"European Application Serial No. 09761163.6, Amendment filed Dec. 9, 2010", 5 pgs.
"European Application Serial No. 09761163.6, Extended European Search Report dated Dec. 14, 2012", (Dec. 14, 2012), 7 pgs.
"European Application Serial No. 09761163.6, Office Action mailed Aug. 21, 2012", 2 pgs.
"European Application Serial No. 09761163.6, Response filed Oct. 31, 2013 to Office Action mailed Aug. 21, 2012", 10 pgs.
"European Application Serial No. 08849716.9, Extended European Search Report mailed Nov. 8, 2011", 8 pgs.
"European Application Serial No. 08849716.9, Office Action mailed Jun. 29, 2010", 2 pgs.
"European Application Serial No. 08849716.9, Office Action mailed Nov. 25, 2011", 1 pg.
"European Application Serial No. 08849716.9, Response filed Aug. 5, 2010 to Office Action mailed Jun. 29, 2010", 135 pgs.
"European Application Serial No. 10769161.0, Amendment filed Dec. 1, 2011", 4 pgs.
"European Application Serial No. 10769161.0, Office Action mailed Jan. 21, 2014", 1 pg.
"European Application Serial No. 10769161.0, Response filed Jul. 30, 2014 to Office Action mailed Jan. 21, 2014", 11 pgs.
"European Application Serial No. 10769161.0, Supplementary European Search Report mailed Jan. 3, 2014", 7 pgs.
"European Application Serial No. EP08849716.9, Response filed Jun. 1, 2012 to Office Action mailed Nov. 25, 2011", 9 pgs.
"European Application Serial No. EP08849716.9, Response filed Sep. 14, 2015 to Summons mailed Mar. 20, 2015", 7 pgs.
"European Application Serial No. EP08849716.9, Summons mailed Mar. 20, 2015", 7 pgs.
"International Application No. PCT/AU2009/000727, International Preliminary Report on Patentability dated Dec. 14, 2010", 10 pgs.
"International Application No. PCT/AU2009/000727, International Search Report and Written Opinion mailed Sep. 30, 2009", (Sep. 30, 2009), 15 pgs.
"International Application No. PCT/AU2010/000511, International Preliminary Report on Patentability dated Nov. 1, 2011", 16 pgs.
"International Application No. PCT/AU2010/000511, International Search Report and Written Opinion mailed Sep. 8, 2010", (Sep. 8, 2010), 23 pgs.
"Japanese Application No. 2011-512783, Office Action Summary", (English Translation), (2013), 2 pgs.
"Japanese Application No. 2012-507546, Office Action mailed Dec. 20, 2013", (English Translation), (2013), 2 pgs.
"Japanese Application U.S. Appl. No. 2014-148142, Office Action mailed May 26, 2015", (English Translation), 3 pgs.
"Machine Translation of JP 06-109631, published Apr. 22, 1994", 9 pgs.
"Machine Translation of JP 11-295233A, published Oct. 29, 1999", 4 pgs.
"Machine Translation of JP 11-304582A, published Nov. 5, 1999", 5 pgs.
"Machine Translation of JP 2001-331878, published Nov. 30, 2001", 7 pgs.
"Machine Translation of JP 2003-281643A, published Oct. 3, 2003", 4 pgs.
"Machine Translation of JP 2004-104727A, published Apr. 2, 2004", 4 pgs.
"Machine Translation of JP 2004-325211A, published Nov. 18, 2004", 12 pgs.
"Machine Translation of JP 2005-115970, published Apr. 28, 2005", 18 pgs.
"Machine Translation of JP 2005-504300A, published Feb. 10, 2005", 7 pgs.
"Machine Translation of JP 2007-057360A, published Mar. 8, 2007", 4 pgs.
"Machine Translation of JP 2007-179266A, published Jul. 12, 2007", 6 pgs.
"Machine Translation of JP 2007-533966A, published Nov. 22, 2007", 4 pgs.
"Machine Translation of JP 2007-533971A, published Nov. 22, 2007", 5 pgs.
"Taiwan Application No. 099114049, office action mailed 2014", (2014), 7 pgs.
"Taiwan Application Serial No. 099114049, Office Action dated Jul. 3, 2014", (w/ English Translation), (Jul. 16, 2014), 12 pgs.
Wang, J. C., et al., "In situ particle size measurements using a two-color laser scattering technique", Applied Optics, 25(5), (1986), 653-657.
"U.S. Appl. No. 14/318,033, PTO Response to Rule 312 Communication mailed Dec. 31, 2015", 2 pgs.
"U.S. Appl. No. 14/318,033, Supplemental Notice of Allowance mailed Jan. 20, 2016", 2 pgs.
"U.S. Appl. No. 14/738,371, Final Office Action mailed Feb. 18, 2016", 17 pgs.
"U.S. Appl. No. 14/738,371, Response filed Apr. 18, 2016 to Final Office Action mailed Feb. 18, 2016", 17 pgs.
"U.S. Appl. No. 14/738,371, Response filed Dec. 16, 2015 to Non Final Office Action mailed Jul. 16, 2015", 10 pgs.
"English Translation of JP 56-132692, published Oct. 7, 1981", 8 pgs.
"Japanese Application Serial No. 2014-225974, Office Action mailed Oct. 6, 2015", (w/ English Translation), 8 pgs.
"Machine Translation of JP 11-339156A, published Dec. 12, 1999", 11 pgs.
"U.S. Appl. No. 14/738,371, Notice of Allowance mailed May 13, 2016", 9 pgs.
"U.S. Appl. No. 15/246,990, Preliminary Amendment filed Sep. 9, 2016", 5 pgs.

* cited by examiner

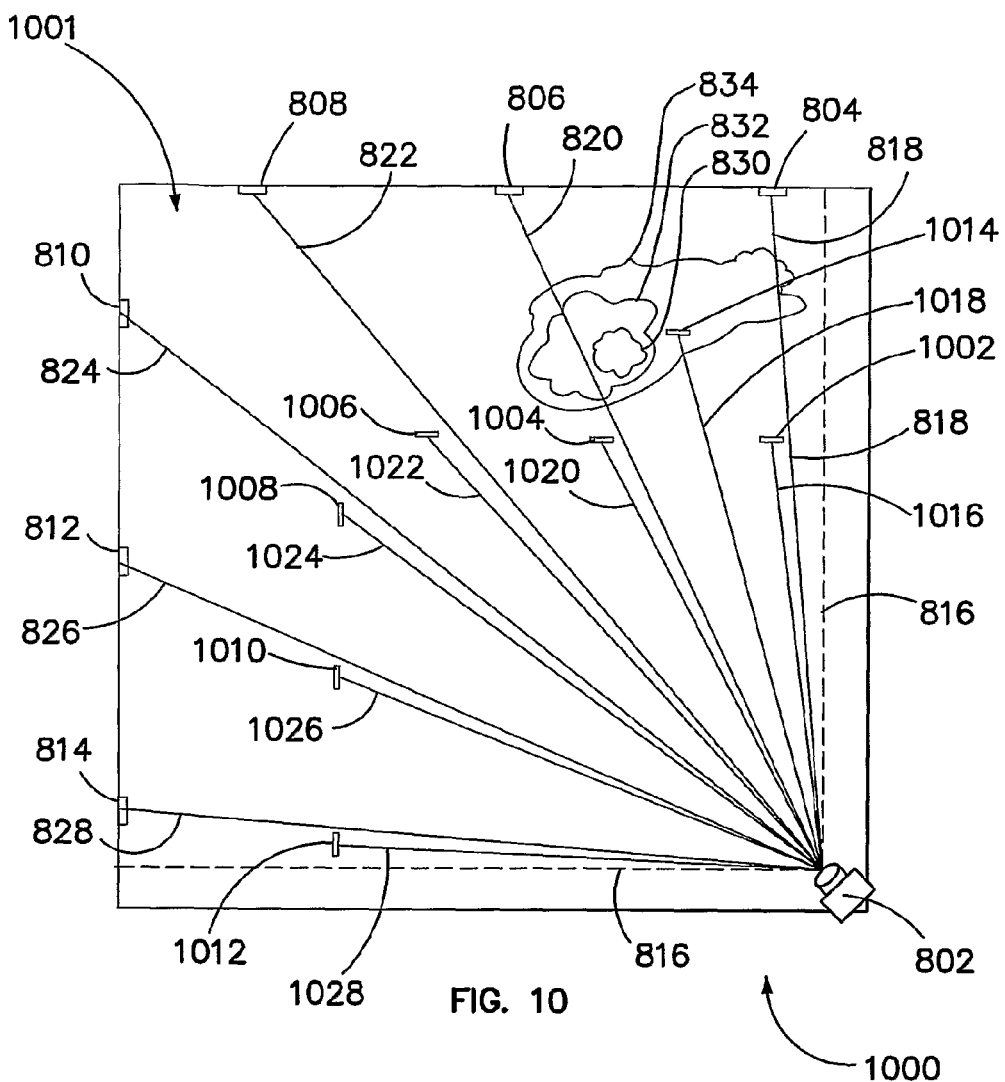
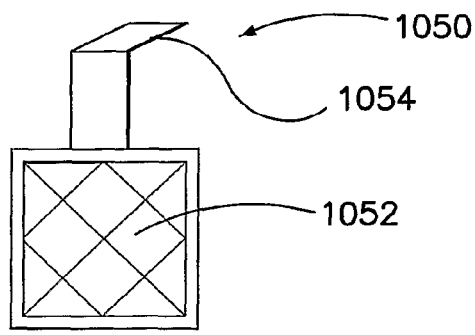
FIG. 10
FIG. 10A

PARTICLE DETECTION

PRIORITY CLAIM TO RELATED APPLICATIONS

This application is a continuation of and claims the benefit of priority to U.S. application Ser. No. 14/318,033, filed Jun. 27, 2014, which application is a continuation of and claims the benefit of priority to U.S. application Ser. No. 12/997,155, filed Dec. 9, 2010, which application is a national stage application under 35 U.S.C. §371 of PCT/AU2009/000727, filed Jun. 10, 2009, and published as WO 2009/149498 A1 on Dec. 17, 2009, which claims priority to Australian Application No. 2008902909, filed Jun. 10, 2008, and to Australian Application No. 2008903268, filed Jun. 26, 2008, and to Australian Application No. 2008903269, filed Jun. 26, 2008, and to Australian Application No. 2008903270, filed Jun. 26, 2008, and to Australian Application No. 2009901923, filed May 1, 2009, which applications and publication are incorporated herein by reference and made a part hereof in their entirety, and the benefit of priority of each of which is claimed herein.

FIELD OF THE INVENTION

The present invention relates to particle detection. It will be convenient to hereinafter describe the invention in the context of smoke detection, however it should be appreciated that the present invention is not limited to that use.

BACKGROUND OF THE INVENTION

Various methods of detecting particles in air are known. One method of detecting the presence of particulate matter in air involves projecting a beam across a monitored area and measuring the attenuation of the beam. Such detectors are commonly known as 'obscuration detectors', or simply 'beam detectors'.

An exemplary, conventional beam detector is shown in FIG. 1. The detector 100 includes a light emitter and detector 102 and a reflector 104 placed either side of a monitored area 106. Incident light 108 from the light emitter and detector 102 are projected toward the reflector 104. The reflector 104 reflects the incident light 108 as reflected light 110. Reflected light 110 is reflected back toward the light source and detector 102. If particulate matter enters the monitored area 106, it will attenuate the incident light 108 and reflected light 110 and cause the amount of light received at the light source and detector 102 to diminish. An alternative beam detector omits the reflector and directly illuminates the detector with the light source across the monitored area 106. Other geometries are also possible.

Whilst the mechanism of smoke detection used by beam detectors is sound, beam detectors commonly suffer from a number of problems.

Firstly, beam detectors may suffer a type I (false positive) error where foreign objects or other particulate matter, such as dust, enters the monitored area and obscure the beam. Beam detectors are generally unable to distinguish between the obscuration caused by particles of interest e.g. smoke, and absorption which results from the presence of foreign body of no interest e.g. a bug flying into the beam.

Secondly, beam detectors may require careful alignment at the time of installation. Such alignment aims to ensure that in normal conditions, free from smoke, light enters the sensor so as to capture the majority of the transmitted beam, and to in turn maximise sensitivity to an obscuration. This calibration may be slow and therefore costly to perform. Moreover, it may need to be repeated as the physical environment that the detector occupies changes, for example because of small movements in the structure to which a beam detector is attached. In some cases, if the intensity of incident light on the detector diminishes quickly this misalignment may also cause a false alarm.

One way of compensating for the second problem is to introduce a photodetector having a high sensitivity over a wide range of incident angles. This reduces the effect that poor alignment between the beam and photodetector would otherwise have. However, this solution comes at the cost of increased sensitivity to unwanted background light, which in turn complicates the detection process and increases the likelihood of failing to detect the presence of particles of interest.

Supplying power to the transmitters within a particle detection system can be costly. There are practical/commercial limits on the amount of power that can be supplied. The limited supply of power limits the optical power output of the transmitter, which in turn limits the signal to noise ratio of the measured signal. If the signal to noise ratio of the system degrades too far, the system may experience frequent or continual false alarms.

In some systems, the signal to noise ratio can be enhanced by employing long integration or averaging times at the receiver. However system response times, which are usually between 10 and 60 seconds, must be increased to higher levels if long integration times are used. This is undesirable.

SUMMARY OF THE INVENTION

In a first aspect the present invention provides a particle detection system including; at least one light source adapted to illuminate a volume being monitored at at least two wavelengths; a receiver having a field of view and being adapted to receive light from at least one light source after said light has traversed the volume being monitored and being adapted to generate signals indicative of the intensity of light received at regions within the field of view of the receiver; a processor associated with the receiver adapted to process the signals generated by the receiver to correlate light received at at least two wavelengths in corresponding regions within the field of view of the receiver and generate an output indicative of the relative obscuration of the light at the two wavelengths.

In one other aspect the present invention provides a particle detection system including; at least one light source adapted to illuminate a volume being monitored at at least two wavelengths; a receiver adapted to receive light from at least one light source after traversing the volume being monitored and to generate an output that spatially and spectrally resolves the received light; a processor to correlate light received at at least two wavelengths in corresponding spatial positions and generate an output indicative of the presence of particles in the volume being monitored.

Preferably the receiver includes a sensor having plurality of sensor elements. It can also include and image forming optics to form an image including the at least one light source.

The light source can include a one or more of light emitters adapted to emit light at a respective wavelength. A light source can emit at a single wavelength only, or a plurality of wavelengths.

The light source can illuminate the volume being monitored at each of the at least two wavelengths at different times. Alternatively the light source can include a light emitter adapted to emit light over a broad wavelength band including the at least two wavelengths simultaneously.

Preferably the particle detection system includes a plurality of light sources.

The processor can be adapted to determine a relative intensity of light received at at least two wavelengths in corresponding spatial positions and generate an output indicative of the presence of particles in the volume being monitored.

The commissioning of such a system can include approximately aligning the light source(s) and receiver such that the at least one light source illuminates the receiver, and selecting in the image sensor which spatial position corresponds to the light source and will be used for measuring received light intensity measurements corresponding to the light source. As the geometry of the system will drift over time the processor preferably tracks which which spatial position corresponds to the light source over time.

The beam of light can be formed using a light source located remotely from the light sensor and positioned to emit light at one or more wavelengths across the monitored region. The beam of light can be formed with one or more reflective targets adapted to reflect a beam of light from a light emitter across the monitored region. In this arrangement the light emitter can be mounted nearby the light sensor and the reflective target located remotely.

A system can include a plurality of beams received on a common light receiver.

In another aspect the present invention provides a beam detector for detecting particles of interest within a monitored volume, said detector including: at least one light source for projecting light across a monitored region, said light including a plurality of wavelengths including at least a first wavelength which is relatively unaffected by particles of interest, and at least a second wavelength that is affected by at least said particles;

a receiver for receiving at least a portion of said projected light and output a signal indicative of an intensity of light received from said light source at at least the first and second wavelengths; and a controller adapted to process the output of the receiver at at least one of the first and second wavelengths and provide an output indicative of whether particles of interest are detected in said monitored region.

Of course, it will be understood that "first wavelength" and "second wavelength", may indicate a wavelength component that is emitted by of a broad spectrum radiation emitter but can also be used to denote a relatively narrow wavelength band by reference to one wavelength within it (usually the central wavelength) such as would be emitted by an emitter with a narrow passband like a laser diode or LED etc, e.g. a first wavelength band may be in the infrared and be centred at 850 nm and have a bandwidth of 50 nm.

As will be appreciated, whilst the illustrative examples relate to the use of visible or near visible electromagnetic radiation the tem light can be seen as broadly encompassing the electromagnetic spectrum. However in the visible and near visible portions of the EM spectrum the challenges in practically and cheaply generating, controlling, focusing and receiving are minimised.

In this way the received light level at the first and second wavelengths can be used to distinguish between the presence of particles of interest and changes in received light levels caused by other factors.

The light source can selectively (e.g. temporally, spatially or spectrally) project light at the at least two wavelengths. Alternatively, the light source can project a light with a wide bandwidth, e.g. white light, that includes light at least the first and second wavelengths. In a system with a wide bandwidth light source the receiver may cooperate with coloured filters to receive and discriminate between the at least two wavelengths.

Preferably the relative intensity of the received light level at the at least two wavelengths is determined e.g. the ratio or difference between them. In the event that the relative intensity of light remains substantially the same, a change in the received light level can be attributed to a factor other than the presence of particles of interest in the monitored region. If a fault condition is met a fault can be signaled.

In the event that a change in received light level at one or both wavelengths causes the relative intensity of light to change in a predefined manner the change in received light level can be attributed to the presence of particles of interest in the monitored region. If an alarm condition is met, a particle detection alarm can be raised.

Preferably the first wavelength is in the infrared portion of the electromagnetic spectrum. The second wavelength is preferably in the ultraviolet portion of the electromagnetic spectrum.

The illumination at the first and second wavelengths is preferably performed alternately. The alternating illumination can be interspersed with periods of no illumination.

In another embodiment a second alarm condition that is determined on the basis of the received light level at one or both wavelengths is also defined such that, in the event that a change in received light level at one or both wavelengths does not cause the relative intensity of light to change in manner that causes the first alarm condition to be met, the second alarm condition can be met.

Preferably the second alarm condition is based on the value of the received light level at one or both wavelengths. Most particularly the second alarm condition compares value of the received light level at one or both wavelengths to a threshold. The second alarm condition can be determined on the basis of the rate of change of the received light level at one or both wavelengths.

This aspect of the invention also provides a method of detecting particles in a region being monitored, including:

emitting light including a first and second wavelength into the region being monitored; the first wavelength being a wavelength whose transmission across the monitored region is relatively unaffected by particles of interest and the second being a wavelength whose transmission across the monitored region is affected by particles of interest;

receiving light at at least a first and second wavelengths after traversing the region being monitored and generating a signal indicative of the intensity of the received light at at least the first and second wavelength;

processing the signal indicative of the intensity of the received light at at least the first and second wavelength to provide an output indicative of whether particles of interest are detected in said monitored region.

The step of processing the signal indicative of the intensity of the received light at at least the first and second wavelength can be based on a change in the relative intensity of the light received at the first and second wavelengths.

In the event that the relative intensity of light at at least the first and second wavelength changes in a predetermined manner an output indicating the presence of particles of interest in said monitored region can be made. Preferably the changes in relative intensity at the two wavelengths are compared to a threshold and if the change in relative obscuration exceeds the threshold an alarm condition is indicated. The threshold can be user selected but is preferably reflects a difference in obscuration at the two wavelengths of between 10% and 50%.

In the event that the relative intensity of the light received at the first and second wavelengths remains substantially stable but an absolute intensity of the light received at one or more of the wavelengths meets one or more predetermined criteria an output indicating the presence of particles of interest in said monitored region can be made.

Another aspect of the present invention provides a beam detector including means for projecting light across a monitored region; means for receiving said light; and processing means; said means for receiving being adapted to discriminate between at least two wavelengths within said light; the processing means being configured to provide a signal indicative of particles in the monitored region in response to a relative intensity of received light at the at least two wavelengths; and the processing means providing a signal indicative of particles in the monitored region in response to a received light level at at least one wavelength, preferably one of the at least two wavelengths.

This aspect of the present invention also provides a method of detecting particles in a monitored region; including:
  measuring a received light level at at least two wavelengths to determine particle concentration,
  determining whether at least one first particle detection criteria is satisfied based on a relative intensity of received light at the at least two wavelengths, and
  determining whether at least one second particle detection criteria is satisfied based on a received light level at at least one wavelength.

In a further aspect the present invention provides a receiver for a particle detection system, said receiver having a field of view and being adapted to receive light at at least two wavelengths, from at least one light source, which has traversed the volume being monitored, the receiver being configured to generate signals indicative of the intensity of the received light at region within the field of view corresponding to each light source at at least one or a plurality of the wavelengths. The receiver preferably has an associated processor configured to process the signal indicative of the intensity of the received light at two or more wavelengths to determine the relative obscuration of the light received from the at least one light source at the two wavelengths. The receiver can include a sensor having plurality of sensor elements each adapted to receive light from a respective region within the field of view of the receiver, e.g. a video camera or similar imaging device. The receiver can receive light from a light source at at least two wavelengths in the same region. Alternatively the receiver could receive light from two light sources at different wavelengths in different regions, and determines the relative obscuration of the light received from the two light sources at the different wavelengths.

In a further aspect the present invention provides a receiver for a particle detection system, the receiver including a light sensor, the light sensor having field of view and being capable of distinguishing light received from a plurality of regions within the field of view at two or more wavelengths; and a processor adapted to receive, from the light sensor, data representing received light and to identify at least one region of the plurality of regions, in which light from a respective one of one or more light sources is received; said processor providing a signal indicative of particles in the monitored region on the basis of the relative level of received light at at least two wavelengths in the identified region of the plurality of regions.

Preferably the processor is adapted to update said identification of the at least one region over time. Preferably the light sensor includes a plurality of light sensor elements, e.g. pixels, each of which correspond to a respective region of the field of view. The processor can be adapted to identify a subset including one or more light sensor elements at which light from the light source is received. The processor may process the received data at successive time periods and track changes in the subset of the sensor elements corresponding to one or more light sources over time.

Advantageously, this arrangement can possess the advantage of a wide field sensor in terms of ease of alignment, and the advantage of narrow viewing angle sensors in terms of receiver noise.

The commissioning of such a system can include approximately aligning the beam and the light sensor, such that the beam falls on the sensor, and performing an image sensor element selection process to determine which image sensor elements will be used for taking received light intensity measurements. As the geometry of the system will drift over time the processor can track which image sensor element(s) are receiving the beam over time.

The beam of light can be formed with one or more reflective targets adapted to reflect a beam of light from a light emitter across the monitored region. In this arrangement the light emitter can be mounted nearby the light sensor and the reflective target located remotely. Indeed the receiver may include one or more transmitters for projecting light toward one or more reflective targets, said targets forming said light sources.

A system can include a plurality of beams received on a common light sensor.

Each light source may include one or more bandpass filters to selectively emit light in chosen wavelength bands.

This aspect of the invention also provides a particle detection system including such a receiver and at least one light source for cooperating with the receiver to define at least one beam detector. Preferably the system includes at least one other beam detector and control means (which may be wholly or partly formed by the processor) configured to:
  detect particles using the first beam detector;
  determine if particles are detected by at least one other beam detector; and
  determine the location of the detected particles on the basis of said determination and the relative positions of first the first beam detector and the at least one other beam detector.

The at least two beam detectors could simply be two light sources cooperating with a common receiver.

Preferably, in the event that particles are also detected by the at least one other beam detector the location of the particles is determined to be a region monitored by both beam detectors.

In the event that particles are not detected by the other beam detectors the location of the particles is determined to be a region monitored by the first beam detector but not the other beam detectors.

Preferably the beam detectors are arranged such that at a plurality of locations in the region being monitored by the system are monitored by at least two beam detectors.

The system can include a plurality of beam detectors arranged to monitor intersecting regions.

Most preferably the particle detection system includes a first receiver adapted to monitor obscuration of a plurality of beams to thereby define a corresponding plurality of beam detectors.

In one embodiment the system includes two receivers each monitoring a plurality of beams to thereby define two groups of beam detectors, and wherein at least one of beam detectors of each group monitor a common location. Preferably each beam of each group monitors at least one location monitored by a beam detector of the other group.

The particle detection system can include beam detectors having beam paths with differing lengths. Preferably at least two beam detectors are arranged next to each other such that their lengths overlap to enable a location of particle detection, along the length of the beam of the first detector, to be determined Preferably the particle detection system includes a light receiver adapted to receive a plurality of light beams. The detection system can include a plurality of light receivers adapted to receive a respective plurality of light beams.

Preferably the light receivers and beams are arranged such that one or more beams pass nearby at least one other beam at known locations to enable localisation of a particle detection event to one of such locations in the event that particles are detected on at least one pair of beams.

This aspect of the invention also provides a method of commissioning a particle detector including a plurality of light sources and a light receiver, the light receiver including a light sensor, the light sensor having field of view and being capable of distinguishing light received from a plurality of regions within the field of view; the method including: arranging the light receiver such that the plurality of light source are in the field of view of the light receiver; and identifying, on the basis of the output of the light receiver, at least one region of the plurality of regions, in which light from a respective at least two of one or more light sources is received to define a plurality of notional beam detectors and independently determining whether particles are detected using each of the notional beam detectors.

The method can include allocating an address on a fire alarm system corresponding to each the notional beam detector defined by a light source in the field of view of the receiver and the receiver.

The method can include positioning one or more reflectors, the reflectors forming light sources and being adapted to reflect light from a light emitter.

In a further aspect the present invention provides a particle detection system incorporating a plurality of beam detectors each having a respective beam transmitted along a corresponding beam path, and wherein the beam paths of at least two of the beam detectors have a region of substantial coincidence, such that in the event that particles are detected in two beams the position of the detected particles can be determined to be within the region of substantial coincidence.

Preferably, in the event that particles are detected in one of the two beams, but not the other, the position of the detected particles can be determined to be at a position within the beam on which detection occurred, but outside the region of substantial coincidence.

In one exemplary system the region of substantial coincidence of two beams is a crossing point of the beams. Alternatively the beams can project parallel to each other and overlap for part of the length of one of at least one of the beams, and the region of substantial coincidence can be the region where the beams overlap.

Preferably the plurality of beam detectors shares either a light source or a light receiver.

In any of the above embodiments more than one spatially separated light sources, reflectors or beams can be used.

In another aspect there is provided a particle detector configured to detect particles of interest in a region being monitored, the detector including:
  remote illumination means adapted to emit light at one or more first wavelengths to illuminate at least part of the region being monitored;
  second illumination means adapted to emit light at one or more second wavelengths to illuminate at least part of the region being monitored;
  a receiver configured to receive a portion of the emitted light at the first and second wavelengths after traversing the region being monitored, said receiver being substantially co-located with the second illumination means; and
  at least one reflector located remotely from the receiver and arranged to reflect the light emitted from the second illumination means to the receiver.

Preferably the reflector and remote illumination means are substantially co-located. Most preferably they are housed in a common device.

Preferably the receiver and the second illumination means are housed in a common device.

The remote illumination means is preferably battery powered. The illumination means preferably includes one or more light sources. Most preferably the light sources are LEDs.

The system can include a plurality of either remote illumination means and/or reflectors.

In another aspect the present invention provides a device incorporating remote illumination means and reflector for use in such a system.

A light source for a particle detection system, said light source including at least one emitter light emitter adapted to project a beam of light; housing supporting the light emitter and mounting means enabling attachment of the housing to a support structure, the mounting means being coupled to the housing such that the orientation of the housing can be changed with respect to the support structure on which the light source is supported.

The light source or receiver can additionally include an indicator for indicating the relative orientation of the direction of projection of the light beam and either or both of: the support structure on which the light source is supported; or an axis of the mounting means.

The indicator can include a dial having one portion indicating angular orientation with respect to an axis of the mounting means and another portion indicating angular orientation with respect to the direction of projection of the light beam.

The light source or receiver can be configured to cooperate with removable sighting means to be used for alignment of the light source with respect to the receiver.

A method of indicating alignment of a light source and a receiver in a beam detector, said light source being configured to emit two partially overlapping beams of light to be received by the receiver, the method including:
  modulating a first beam of the overlapping beams of light with a first modulation scheme;
  modulating a second beam of the overlapping beams of light with a second modulation scheme that is distinguishable from the first modulation scheme;
  receiving light from the light source;
  determining the relative alignment of the light source and the receiver in the basis of a modulation scheme detected in the received light.

Preferably the method includes indicating correct alignment of the light source and receiver if a component of the received light is modulated according to the each of the first and second modulation schemes.

Preferably the method includes indicating misalignment if the received light is modulated according to only one of the first and second modulation schemes.

A method of detecting a condition of a light source of a particle detection system which emits a beam of light received by a receiver, said method including:
- modulating the illumination of the light source according to a predetermined modulation scheme:
- varying the modulation scheme in the event that a predetermined condition exists in the light source;
- detecting the variation in the modulation scheme in the light received by the receiver.

Preferably the condition indicated is a low battery condition in the light source.

The method can include intermittently varying the modulation scheme between the predetermined modulation scheme and the varied modulation scheme.

A method for detecting particles in a region, comprising;
- providing a receiver having a field of view insufficient to view the entire region;
- forming a plurality of beams projecting across the region towards the receiver;
- changing the orientation of the field of view of a receiver to monitor a plurality of the beams; and
- determining whether particles are present in the region on the basis of each the level of light received from each received beam.

The step of forming a plurality of beams projecting across the region towards the receiver can include projecting beams across the region to coincide with field of view of a receiver as it changes. The beams can be formed directly by a light source or by reflecting a light source from a reflector.

In a preferred form the method includes scanning the field of view through a predetermined angle to sequentially receive light from a plurality of beams. The method can include scanning a light source across the region in time with the field of view of the receiver, and receiving light beams reflected from a plurality of reflectors.

In a further aspect the present invention provides a method of monitoring for particles in a region using a particle detector of the type described above, said method including:
- illuminating at least part of the region being monitored using the remote illumination means;
- receiving at least a portion of the emitted by the remote illumination means after traversing the region being monitored, and in the event that the received light level meets at least one predetermined criteria;
- illuminating at least part of the region being monitored using a second illumination means;
- receiving at least a portion of the emitted light at a second wavelength after traversing the region being monitored, and
- determining whether particles are present in the region being monitored on the basis of a received signal at one or both of the wavelengths.

In an aspect the present invention provides a light source for use in a particle detector said light source including:
- a plurality of light emitting elements arranged to project a light beams in respective directions;
- means for selectively illuminating one or more of the light emitting elements such that the light source can be configured to project at least one selected direction.

Preferably the light emitting elements are LEDs.

Preferably the light emitting elements have relatively narrow fields of illumination and are arranged such that light source may have a relatively wide field of illumination. Preferably the field of illumination of each light emitting element at least partially overlaps that of another light emitting element.

A method in a particle detector including a light source of the previous aspect of the present invention to generate a beam of light, the method including:
- determining a desired direction of projection of the beam of light; and
- selectively illuminating one or more of the light emitting elements which project a beam of light in the desired direction.

The method can include, illuminating a one or more of the light emitting elements and monitoring for reception of a beam of light at a receiver; and in the event that a beam of light is not received, selecting another light emitting element for illumination. This step can be repeated until a beam of light is detected.

In the above embodiments each light source can be adapted to generate an illumination at a plurality of wavelengths, preferably two wavelengths, to enable an embodiment of any one of the particle detection methods described herein to be performed.

In the above embodiments a light source can be adapted generate light at two wavelengths according to a modulation scheme. The scheme can include a pulse train which includes at least one pulse of light at a first wavelength and pulse of light at a second wavelength. A plurality of pulses at one or both of the wavelengths can be included in a pulse train. In the event that a plurality of light sources is used the modulation pattern of the light sources may be the same or different. Moreover the modulation pattern of the light sources are preferably not synchronised with each other.

BRIEF DESCRIPTION OF THE DRAWINGS

Illustrative embodiments of the present invention will now be described by way of non-limiting example only with reference to the following figures, in which:

FIG. 10 illustrates a particle detection system with a second addressing scheme according to an embodiment of the present invention;

FIG. 10A illustrates a retroreflective target;

DETAILED DESCRIPTION OF THE EMBODIMENTS

Figure 1:
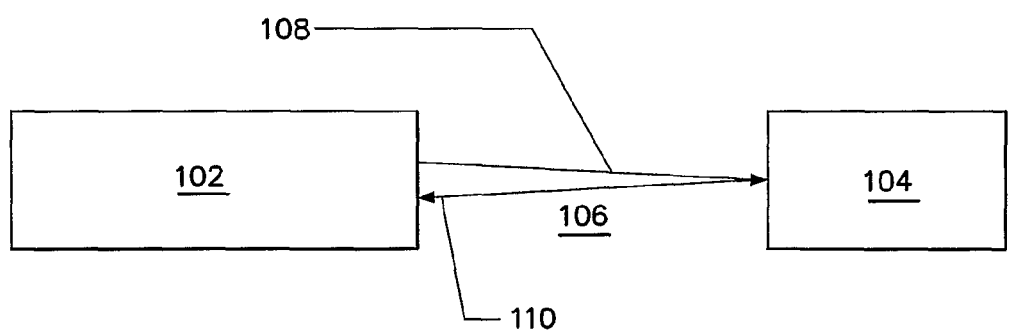
FIG. 1 is a prior art beam detector.
Figure 2:
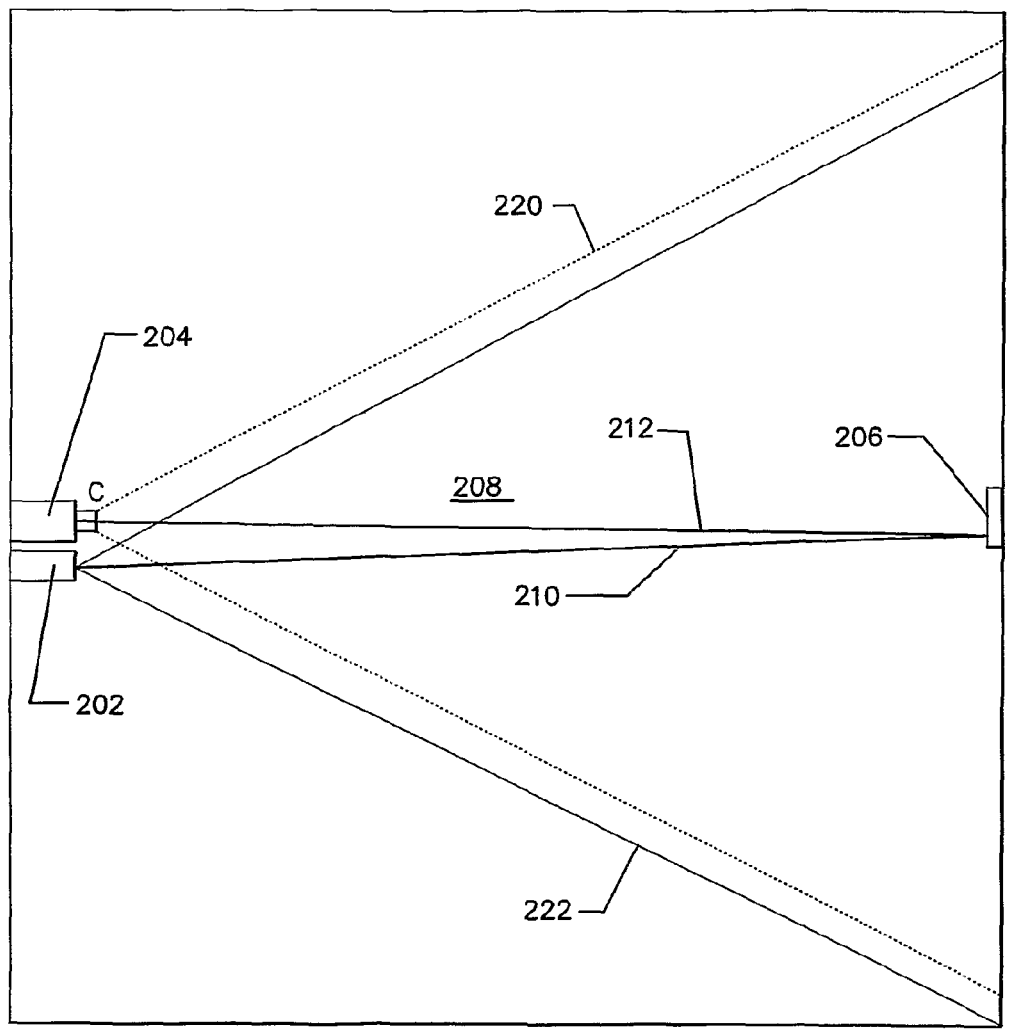
FIG. 2 illustrates a first embodiment of the present invention.

FIG. 2 shows an embodiment of the present invention. The detector 200 includes a light emitter 202, a receiver 204, and a target 206, acting in co-operation to detect particles in a monitored area 208. Target 206 reflects incident light 210 and thereby forms a light source and returns reflected light 212 to receiver 204. Preferably the target is a corner cube or other reflector adapted to reflect light back along its incident path, or other determined path.

The term light source as used is intended to be interpreted to include a device that actively produces an illumination from one or more (generally termed a light emitter or transmitter herein) as well as a reflector of an illumination generated by another device (generally termed a target or reflector herein).

In the preferred embodiment the receiver 204 is preferably a video camera or other receiver having an array of light sensors. A person skilled in the art would appreciate that receiver 204 may be constructed using a range of image sensor types, including one or more CCD (charge-coupled device) image sensors, or CMOS (complementary metal-oxide-semiconductor) image sensors, or indeed any device capable of recording and reporting light intensity at a plurality of points across its field of view, without departing from the spirit of the invention.

Receiver 204 receives all of the light in its field of view 220, and includes imaging optics to form an image of a field of its view 220, including the target 206 on its image sensor. This light includes reflected light 212. Receiver 204 records the intensity of all light in its field of view, in the form of data representing the image intensity at a series of locations throughout the field of view. A portion of this data will correspond, at least partially, to reflected light 212. Receiver 204 communicates the image data to a microcontroller. The microcontroller analyses the image data, and determines which portion of the data provides the best estimate of reflected light 212. Because the receiver 204 has a wide field of view and has the ability to measure light at a wide range of points within this field of view the light emitter 202 need not be carefully aligned with target 206, or with receiver 204, since the effect of a misalignment will simply be that a different portion of data, corresponding to different pixels within the view, will be used a measure of reflected light 212. Accordingly, provided that the field of view of the receiver includes target 206, one or more regions of interest within the image will include a measured value for the reflected light 212. It is noted that additional background or stray light from areas other than the region of interest can be ignored by the microcontroller.

The microcontroller may base its decision, as to which pixels of the image sensor correspond to the reflected light 212 for example, on the relative intensity of a particular part of the image compared with other areas of the image. It may similarly use information gained about the environment, or historically recorded data. At the conclusion of this decision process, the microcontroller will have selected a portion of data, perhaps corresponding to a pixel or group of pixels read from the image sensor, that can most reliably be used to measure the intensity of reflected light 212.

The microcontroller now monitors the regions of the image that it has previously selected as corresponding to the reflected light 212. If smoke or other particulate matter enters monitored area 208, smoke or particulate matter will obscure or scatter incident light 210 or reflected light 212. This obscuration or scattering will be detected as a drop in the intensity for received reflected light 212 measured in the image region determined by the microcontroller.

Pixels falling outside the region selected by the microcontroller, to include the reflected light 212, can be ignored as light received by these pixels does not correspond to the reflected light 212.

Over time, as the building moves or other factors alter the geometry of the system, the target 206 will still be in the field of view of the receiver 204 however, the image of the target 206 will appear at a different point on the image detector of the receiver 204. In order to address this motion of the image of the detector, the microcontroller is adapted to track the image of the target 206 across its light sensor over time to enable a smoke detection to be performed on the correct image regions over time.

Figure 3A:
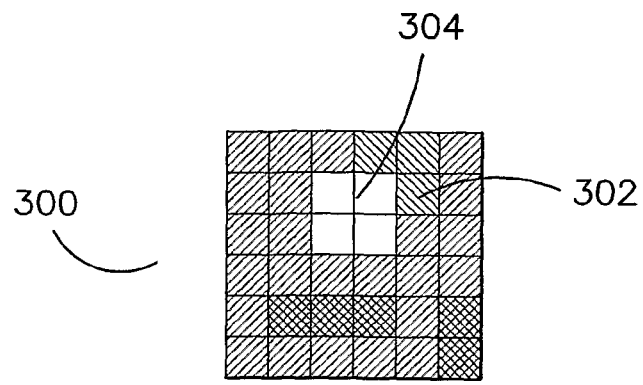
FIG. 3a and FIGS. 3b illustrate schematically an image received at the light sensor of the light receiver 204 of the system in FIG. 2.
Figure 3B:
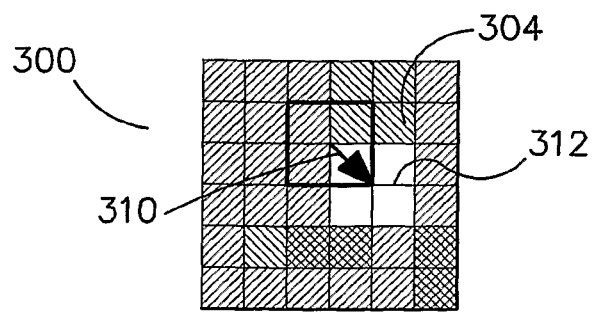

FIG. 3a and FIG. 3b illustrate schematically an image received at the light sensor of the light receiver 204 of the system in FIG. 2 at different times. In this embodiment the output of the sensor enables the received light intensity at a plurality of locations to be determined In one form the sensor is a CMOS imaging chip or similar, and includes a plurality of pixels 302, each pixel corresponding to a position in the field of view 300 of the light receiver. In use, the microcontroller reads out the light intensity of the plurality of the pixels e.g. 302. In any given image frame the light level received varies from pixel to pixel within the array of pixels 300.

By analysing the image, the microcontroller can determine that certain pixels (or a single pixel) correspond to an image of the target 206, which lies with within the field of view of the receiver 204. This group of pixels, labelled 304, has a substantially higher level of received light than the other pixels and corresponds to the received beam transmitted by the light source.

Over time, as the building moves or other factors alter the geometry of the system, the target 206 will still be in the field of view of the receiver 204 however, the image of the target 206 will appear at a different point on the image detector of the receiver 204. In order to address this motion of the image of the detector, the system microcontroller can be adapted to track the image of the target 36 across its light sensor over time to enable particle detection to be performed on the correct image regions over time. FIG. 3b is substantially identical to FIG. 3a with the exception that the "spot" caused by the target in the field of view 300 has moved in a direction indicated by arrow 310.

In one embodiment, tracking of the "spot" can be performed by the microprocessor initially storing in memory a first set of pixel co-ordinates corresponding to the "spot" in the field of view. Periodically, the microcontroller examines the measured value of the pixels within a predetermined distance from the "spot", including the pixels corresponding to the spot. The microcontroller then calculates a second list of pixel co-ordinates by selecting the n-brightest pixels from the said surrounding area. The second list is then compared with the first list, and if the lists differ by more than m-pixel co-ordinate pairs, an error is indicated. If the lists differ by m-less or pixel coordinate pairs, the second list of pixel co-ordinates is stored in place of the first list of pixels.

In an alternative scheme the controller of the system can analyse the received image, and determine which portion of the image contains information most strongly related to a received beam. At the conclusion of this decision process, the controller will have selected two portions of signals that are produced by respective individual sensors or groups of sensors, so the selected signal can most reliably be used to measure the intensity of beams. One way of selecting the sensors whose data can be most reliably used is to view the image generated by the receiver at the time of commissioning the smoke detector and selecting the appropriate sensors.

A further mechanism of ensuring that the calculated received beam intensity is as close to the actual intensity of the received beam as possible can involve the microcontroller deciding whether to use the value corresponding to a certain sensor element, according to that element's contribution to the overall image strength. For example, from the sensor element outputs, the controller can determine a 'centre-of-signal' position of the beam. The centre-of-signal position is analogous to the centre of mass position, except that instead of mass, it is the signal value contributed by each pixel (i.e. sensor element) that is used in the calculation. For example, the following equation may be used:

Centre-of-signal position vector={sum of(position vector of each pixel)*(value of each pixel)}/ {sum of values from all the pixels}.

After the centre-of-signal position is determined, the controller may weight the signal contributed to the received beam intensity value by each sensor element (i.e. corresponding to the electrical signal generated by each sensor) according to the distance between that sensor element. In this way, the controller determines the sensor elements whose signals best represent the target image and that are least likely to be dropped from subsequent measurements due to drift in the beam image's position on the sensor.

In use the microcontroller will compare the intensity of light received within this group of pixels to the light received in an earlier image to determine whether there had been an increase in obscuration of the beam caused by particles in the monitored region 208.

The microcontroller can then use conventional smoke detection methods to determine when smoke is detected and if an alarm should be raised. For example smoke can be detected by monitoring the level of received light, and when a chosen characteristic of the received light meets one or more predetermined criteria it is determined that smoke is present in the volume being monitored. For example, when the received light level falls below a predetermined level it can be determined that smoke is present. Alternatively, when the rate of change of the received light level exceeds a predetermined level it may be determined that smoke is detected. As will be appreciated the smoke detection criteria can also include a temporal condition, e.g. that the received light level must drop below a threshold for more than predetermined period of time before an alarm is raised.

To improve the system's sensitivity, a cancellation algorithm can be used to minimise the effect of background light on the measured received light intensity. One such algorithm operates by alternatively capturing images of the field of view of the receiver with the light source turned on and off. The measured light intensity of the "off" frames (i.e. images captured without illumination) can be subtracted from the "on" frames (i.e. images captured with illumination). Received light that is not attributable to the illumination by the light source background light, can thereby be substantially eliminated.

A person skilled in the art would appreciate that collection of 'off frames' can be achieved in a variety of ways, including by selectively suppressing a light source having a particular wavelength, for example by modulating a control input to the light sources, or alternatively by introducing a filter in front of the source that temporally blocks light having particular wavelengths. Such a person would also appreciate that elimination of background light could be achieved by means other than simple subtraction, for example by use of suitable filter, or by some other computational approach.

Figure 4:
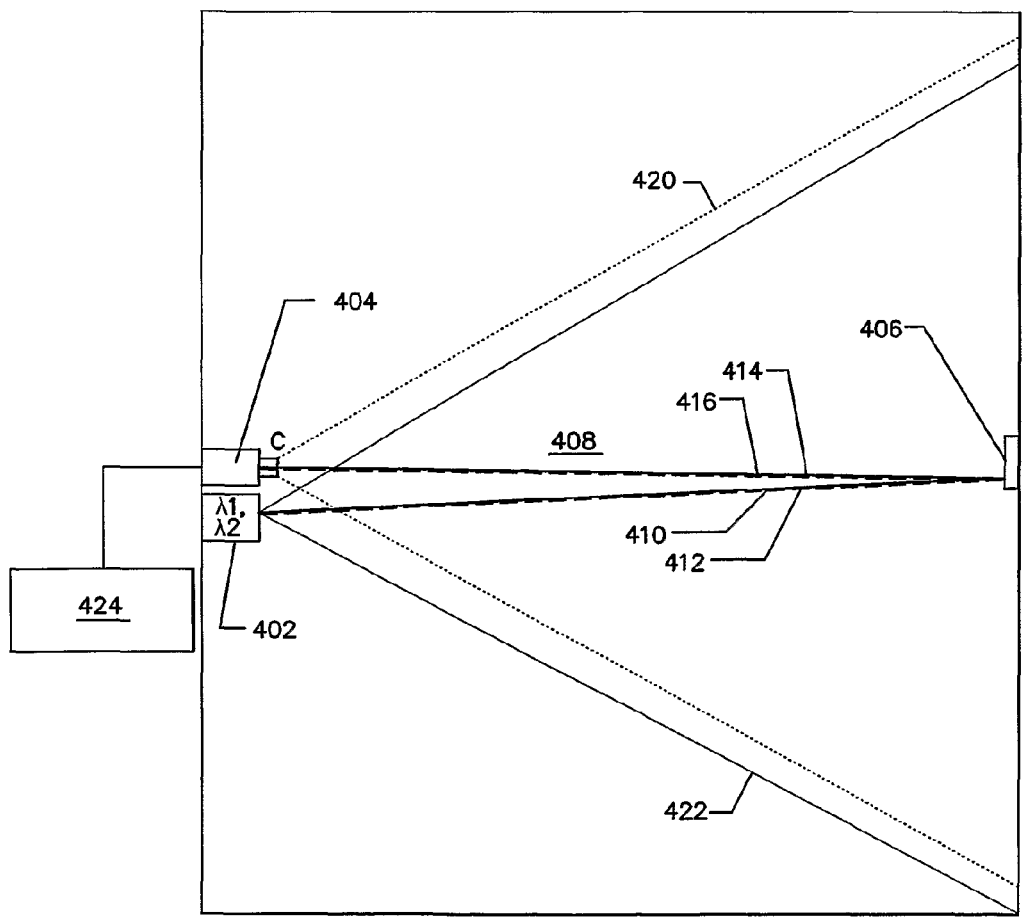
FIG. 4 illustrates a second embodiment of the present invention using two wavelengths of light.

In a preferred embodiment of the present invention the target is illuminated at two (or more) wavelengths. FIG. 4 depicts an embodiment of the present invention having multiple light emitters which emit light at two wavelengths $\square_1$ and $\square_2$. This example includes an infrared (IR) light emitter and ultraviolet (UV) light emitter 402 which emit light along two substantially collinear paths. It also includes a receiver 404, and a target 406, acting in co-operation to detect smoke in monitored area 408. Target 406 reflects incident UV light 410 as reflected UV light 414 and also reflects incident IR light 412 as reflected IR light 416. The two wavelengths are chosen such that they display different behaviour in the presence of particles to be detected, e.g. smoke particles. In this way the relative change in the received light at the two (or more) wavelengths can be used to give an indication of what has caused attenuation of the beam.

Receiver 404 receives both reflected infrared light 416 and reflected ultraviolet light 414, along with other light in its field of view. Receiver 404 records the intensity of all light in its field of view at a series of locations throughout the field of view as described above. A portion of this data will correspond, at least partially, to the intensity of reflected infrared light 414. A portion of this data will correspond, at least partially, to the intensity of reflected ultraviolet light 414. Receiver 404 includes microcontroller 424 for processing image data.

In this system, to apply the background cancellation approach described above, the two light sources emitting at wavelengths $\lambda_1$ and $\lambda_2$ can be configured to operate alternately with short periods of no illumination between, to allow blank frames to be collected. In a simple form of this embodiment, the illumination pattern and receiver can be synchronised to operate as follows:

| Illumination | $\lambda_1$ | off | $\lambda_2$ | off | $\lambda_1$ | Off | $\lambda_2$ |
|---|---|---|---|---|---|---|---|
| Receiver | $\lambda_1$ frame | blank | $\lambda_2$ frame | blank | $\lambda_1$ frame | blank | $\lambda_2$ frame |

Alternatively a more complex system could be implemented that used separate image capture chips for each wavelength, or which uses continuous illumination and selectively filters the received light to generate on and off frames at each wavelength.

Microcontroller 424 analyses the data, and determines which portion of the data contains information most strongly related to reflected ultraviolet light 414 and reflected infrared light 416 respectively as described above.

Particle detection algorithms could then be applied independently on the received UV light and received IR light as described above. However, it is preferred that the two wavelengths are chosen such that they display different behaviour in the presence of particles to be detected, e.g. smoke particles. In this way the relative change in the received light at the two (or more) wavelengths can be used to give an indication of what has caused attenuation of the beam. If the relative obscuration of the received beams drops below a predetermined threshold then an alarm can be raised.

Attenuation of a light beam in air is produced primarily by the effect of some of the light being scattered off-axis due to interaction with airborne particles. UV light is scattered relatively strongly by small particles, e.g. smoke, and IR is scattered less by such particles; thus in a smoke detector the IR beam can be used as a reference beam for the primary UV smoke detection beam. In this example, both the UV and IR beams will be equally sensitive to variations in received intensity that are caused by things like drift in the system, soiling of the optics of the system, a large foreign object passing through the beam (e.g. a bird etc.) or relatively large nuisance particles such as dust, but the UV light will be more severely attenuated by smoke which is typically dominated by small particles. By carefully selecting the wavelengths used in the system the desired particle size selectivity can be chosen. The present examples use an IR wavelength of 850 nm as a reference wavelength, however a longer wavelength such as 1500 nm may be used in some embodiments. Similarly the shorter wavelength beam can be made shorter, say 200 nm to achieve greater sensitivity to smaller particles. Other wavelengths that are either longer or shorter can also be used. However the cost of implementing the emitter and receiver in such systems can make them prohibitive in most applications.

Figure 5A:
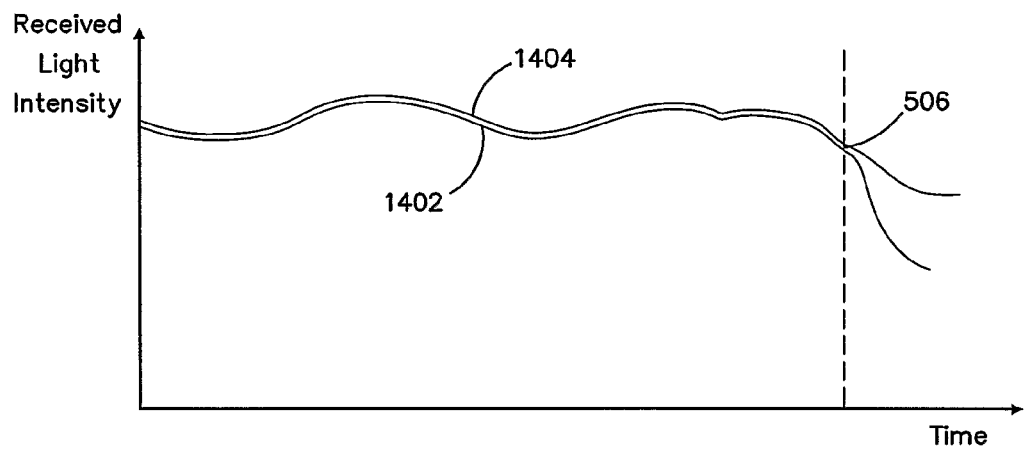
FIGS. 5a and 5b illustrate schematically the operation of the detector of FIG. 4 in two circumstances.
Figure 5B:
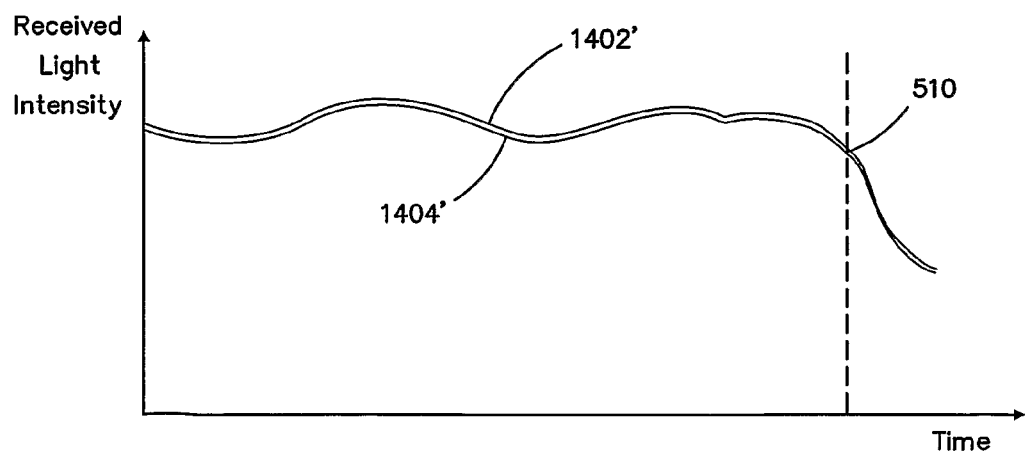

FIGS. 5A and 5B illustrate schematically the received light intensity of a system at two wavelengths over time. In these figures the received light level of UV light is illustrated by curve 1402 and the received light level of IR light is illustrated by curve 1404. Generally, the received light intensity of the two beams vary in a similar manner over time, and hence their ratio will be substantially constant over time. At time 506, the two curves 1402 and 1404 diverge. This indicates that an event has happened that has caused a greater attenuation of the UV beam than the IR beam. Consequently the ratio of received UR and IR radiation will move away from its substantially constant state.

Because of the properties of UV and IR radiation mentioned above, this indicates that small particles, like smoke have entered the beam path and caused attenuation and the microprocessor can be configured to indicate that smoke has been detected.

FIG. 5B illustrates the case where the beam is attenuated by a different cause. At time 510, the received intensity of both beams is greatly reduced. This indicates that the cause of the obscuration is not wavelength dependent and is likely to be either an alignment problem or large foreign body entering the beam.

As can be seen in this simple example, the use of a reference beam and a primary detection beam can allow a distinction to be drawn between a likely particle detection event an another cause of beam attenuation.

The wavelengths of light mentioned here are given as examples only, and the inventors anticipate that other wavelengths could be chosen that could adapt the system to detect certain types of particles. In a particularly preferred embodiment the reference beam would not be absorbed or scattered at all by the particles or interest, but would be attenuated by all other events. In this case the reference beam would give an indication of structural or foreign body effects on the system only.

However, the present inventors have determined that in certain circumstances performing smoke detection at these two wavelengths and then subtracting a received signal at one wavelength from the received signal at the other wavelength, or taking the ratio of received signals at the two wavelengths, may be prone to failure in the presence of certain types of particles or clouds of particles having a certain particle size distribution.

For example, a smoke detection test has been performed on a two wavelength smoke detection system, in which smoke was generated using the following set up. A white cotton towel was closely wrapped around an electrical element and the element and towel placed in a receptacle. When electricity was passed through the element a large amount of smoke was produced. The smoke from this source was introduced to an apparatus measuring light transmission at violet (405 nm) and infrared (850 nm) wavelengths however, it was found that these wavelengths were affected substantially equally, making a smoke detector dependent upon a differential or ratiometric measurement ineffective. In contrast a smoke detector operating at a single infrared wavelength easily detected this smoke.

Figure 11A:
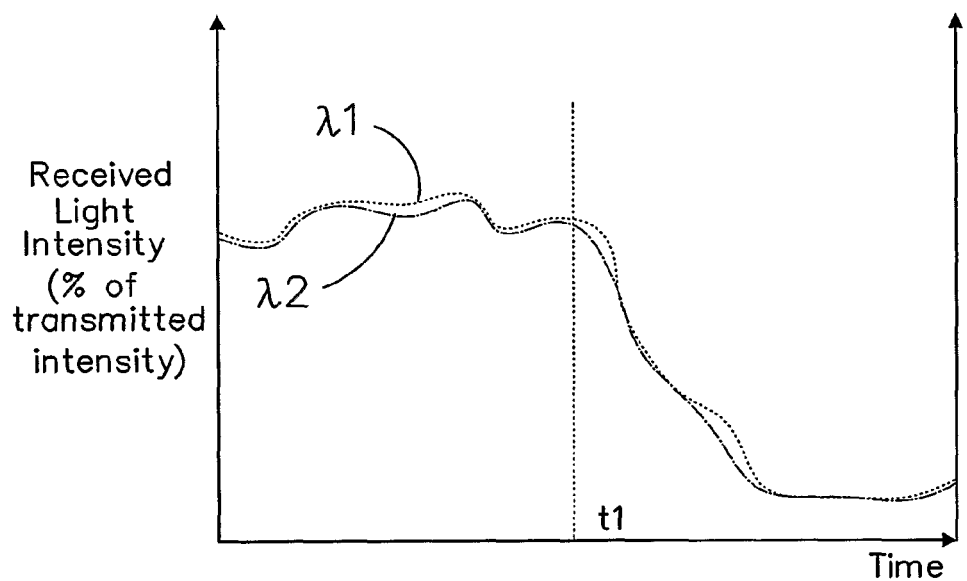
FIG. 11A illustrates a plot of received light intensity for a particle detector operating at two wavelengths when detecting products of combustion demonstrating an unusually high proportion of large particles compared to small particles.

FIG. 11A illustrates an example of a smoke detector response at two wavelengths $\lambda_1$ and $\lambda_2$. As can be seen the received light intensity at two wavelengths varies over time but initially is substantially flat and equal at the two wavelengths. At the time $t_1$ smoke (generated in the manner described above) enters the detector and the received light intensity at each of the wavelengths decreased substantially. However, unlike the case depicted in FIG. 5a the response at both wavelengths $\lambda_1$ and $\lambda_2$ decrease in concert after time $t_1$.

Figure 11B:
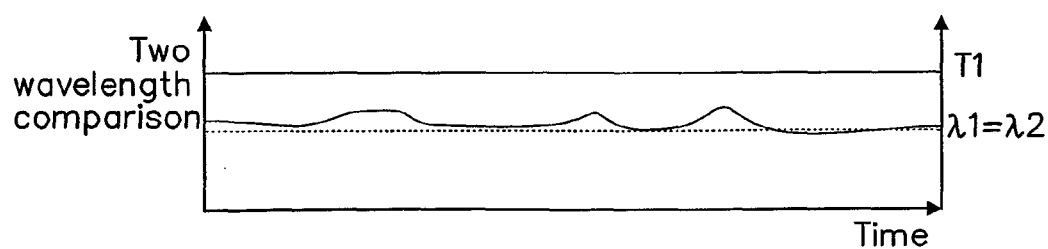
FIG. 11B is a plot of a comparison of detector output at first and second wavelengths corresponding to FIG. 11A.

This trend can be seen in FIG. 11B which indicates a comparison of the output of the smoke detector at two wavelengths $\lambda_1$ and $\lambda_2$ (e.g. $\lambda_1$=405 nm and $\lambda_2$=850 nm) over the same timescale as FIG. 11A. The two wavelength comparison could be any known comparative measure, such as the received light intensity level at $\lambda_2$ subtracted from the received light intensity level at $\lambda_1$, or the ratio of these values, or some other measure. As can be seen, since the responses at $\lambda_1$ and $\lambda_2$ remain substantially the same the comparison curve in FIG. 11B does not vary far from the central position indicating that the response at wavelength $\lambda_1$ is the same as the response at wavelength 2. In the case where the smoke detector is configured to enter an alarm condition when the comparison value reaches a pre-determined threshold, say $T_1$, the situation illustrated in FIG. 11A would not cause an alarm to be raised. In ordinary operation the inventors have determined that a threshold reflecting a change in relative obscuration of between 10% and 50% works well. However the desired threshold level can be set to achieve a balance between false alarms and sensitivity.

The present inventors have devised two methods of addressing the shortcomings, which may be used either alone or together, with the embodiments of a particle detector as described above, or with other types of particle detector, including detectors which detect the presence of particles on the basis of the received scattered light in either a forward or backward scattering geometry) to avoid the abovementioned drawbacks.

In a one exemplary embodiment the present inventors have determined that smoke produced in the manner described above can be better detected using a reference wavelength and that the system can be augmented with a third wavelength light emitter to emit a third beam of light. The inventors have determined experimentally that a beam in a wavelength band centred at about 540 nanometres is unexpectedly unaffected by particles in the smoke test described above.

Figure 12A:
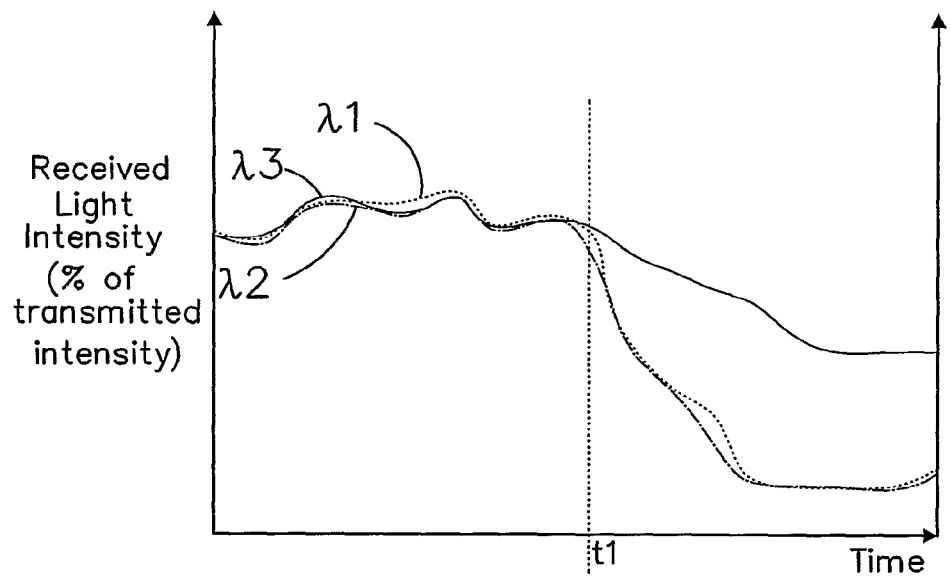
FIG. 12A illustrates a detector output at three wavelengths for products of combustion demonstrating an unusually high proportion of large particles compared to small particles.

FIG. 12A illustrates an illustrative plot of the response of a smoke detector operating at 3 wavelengths indicated as $\lambda_1$, $\lambda_2$, and $\lambda_3$ (e.g. $\lambda_1$=405 nm, $\lambda_2$=850 nm and $\lambda_3$=520 nm) in the presence of smoke generated in the manner described above where is in the green portion of the visible light spectrum. In this case, the plots for $\lambda_1$ and are the same as in FIG. 11A, however, as can be seen the plot for is quite different. In this regard, initially, i.e., before time $t_1$, the plot for $\lambda_1$ is substantially the same as for and $\lambda_2$. The corresponding portion of FIG. 12B, which shows the comparison between the plot of $\lambda_1$ and, $\lambda_3$, is substantially flat and varies closely around the $\lambda_1$=$\lambda_3$ line.

Figure 12B:
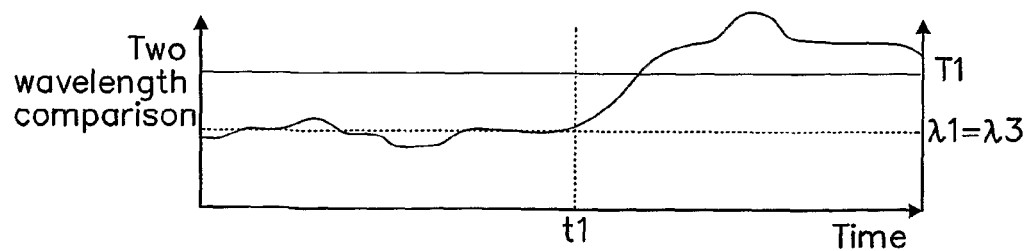
FIG. 12B is a plot of the two wavelength comparison between the first wavelength and the third wavelength from FIG. 12A.

After time $t_1$ at which point the smoke is introduced into the detector, the plots for $\lambda_1$ and $\lambda_2$ drop off together, however the plot for decreases in a much slower fashion. Accordingly, as seen in FIG. 12B the comparison between $\lambda_3$ and $\lambda_1$ increases and eventually crosses the alarm threshold $t_1$. As will be appreciated by those skilled in the art a similar curve would be generated by comparing the $\lambda_3$ response with the $\lambda_2$ response.

Thus, it can be seen that by augmenting a two wavelength system with at least one reference wavelength (e.g. a green wavelength) in a particle detector of the type described herein, particle detection events which may otherwise go undetected may be detected.

In an alternative form, a two wavelength system including either the illumination and only one other colour illumination could be used, rather than a three (or more) wavelength system as described above.

Figure 13:
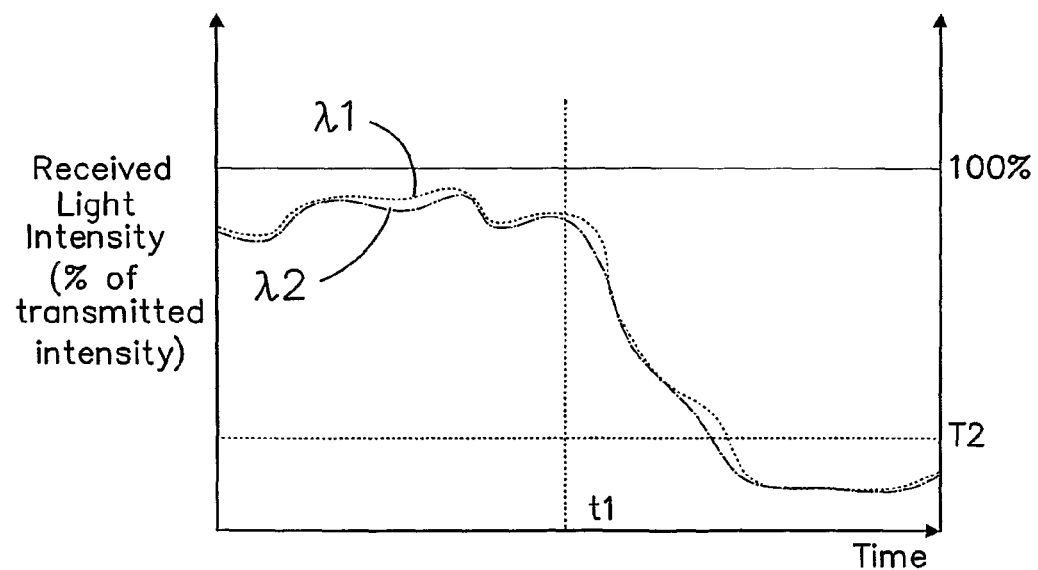
FIG. 13 illustrates how an alarm threshold may be implemented in an embodiment of the present invention.

FIG. 13 illustrates a second mechanism determined by the present inventors which may be used to ameliorate the disadvantages of the prior art in detecting such smoke. This approach is contrary to previous approaches employed in smoke detectors using multiple wavelengths. Certain aspirated or point detectors on the market which use multiple wavelengths of light to detect smoke to either subtract the receiver signal one wavelength from that detected at the other wavelength, or to take a ratio of the output of the smoke detector at the two wavelengths to detect the presence of smoke. However, as can be seen from the above this approach fails to detect smoke when both wavelengths are equally (or proportionately) attenuated. As an illustration, international patent application WO02008/064396 in the name of Siemens Schweiz AG describes a multiple wavelength smoke detector which uses a short wavelength signal to enhance the detection of small particles in the event that the short wavelength response is substantially greater than the long wavelength response. However, in the case where the response at each of the wavelengths is substantially similar e.g. where one response is between 60% and 95% of the response at the other wavelength, the inventors teach that ratio of the responses at the two wavelengths is used. In the presence of products of combustion demonstrating an unusually high proportion of large particles compared to small particles, such as may be generated by heating materials in a restricted air supply, because the response at both of the wavelengths is substantially the same, the detector would always use the comparison measurement and thus never go into alarm and the detector would fail to detect the smoke.

The present inventors have determined that this problem can be overcome by applying a fallback detection threshold which is used to trigger an alarm, irrespective of the value of the comparison between the detector response at the two wavelengths.

Thus in FIG. 13, the threshold $T_2$ is set, and once the received light intensity at either or both of $\lambda_1$ and $\lambda_2$ drops below that threshold an alarm condition is indicated.

Such a threshold may potentially cause false alarms if the smoke detection beam is obscured by a foreign body, however this risk can be minimised by other means, such as by analysing the rate of change of the obscuration signals or applying suitable alarm delays etc. As will be appreciated, a solid body will typically cause a sharp obscuration change, whereas a smoke plume will typically build up somewhat more slowly and have a slower rate of change at each wavelength. Moreover, by averaging the obscuration over a short period of time, transient obscuration, for example as may be caused by a bird flying through the beam, can be largely ignored.

Figure 6:
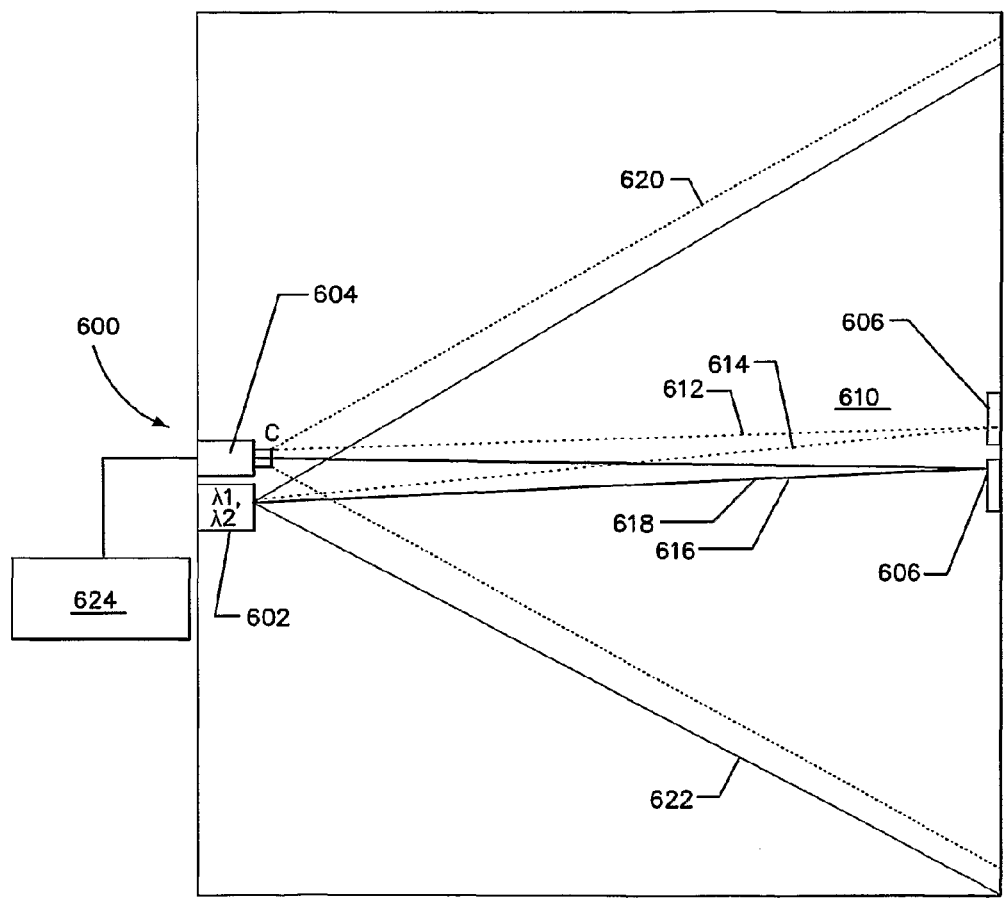
FIG. 6 illustrates a further embodiment of the present invention which includes two targets in the field of view of the receiver.

FIG. 6 depicts an embodiment capable of monitoring multiple targets simultaneously. According to this embodiment, the detector 600 includes a light emitter 602, a receiver 604, a first target 606, and a second target 608 acting in co-operation to detect smoke in monitored area 610. Target 606 reflects incident light 612, resulting in reflected light 614 returning to receiver 604. Target 607 reflects incident light 616, resulting in reflected light 618 returning to receiver 604.

As with the previous embodiment, the receiver 604 includes microcontroller 624 for processing image data. Microcontroller 624 analyses the data, and determines which portion of the data contains information most strongly related to reflected light 614 and reflected light 618 respectively. At the conclusion of this decision process, the microcontroller 624 will have selected two portions of data, corresponding to respective individual pixels or respective groups of pixels read from its image sensor, that can most reliably be used to measure the intensity of reflected light 614 and reflected light 618 respectively.

In this way the system 600 can, by the addition of only an additional target, perform the function of two beam detectors. A person skilled in the art would appreciate that this principle could be extended to include any number of targets and reflected light beams.

Figure 7:
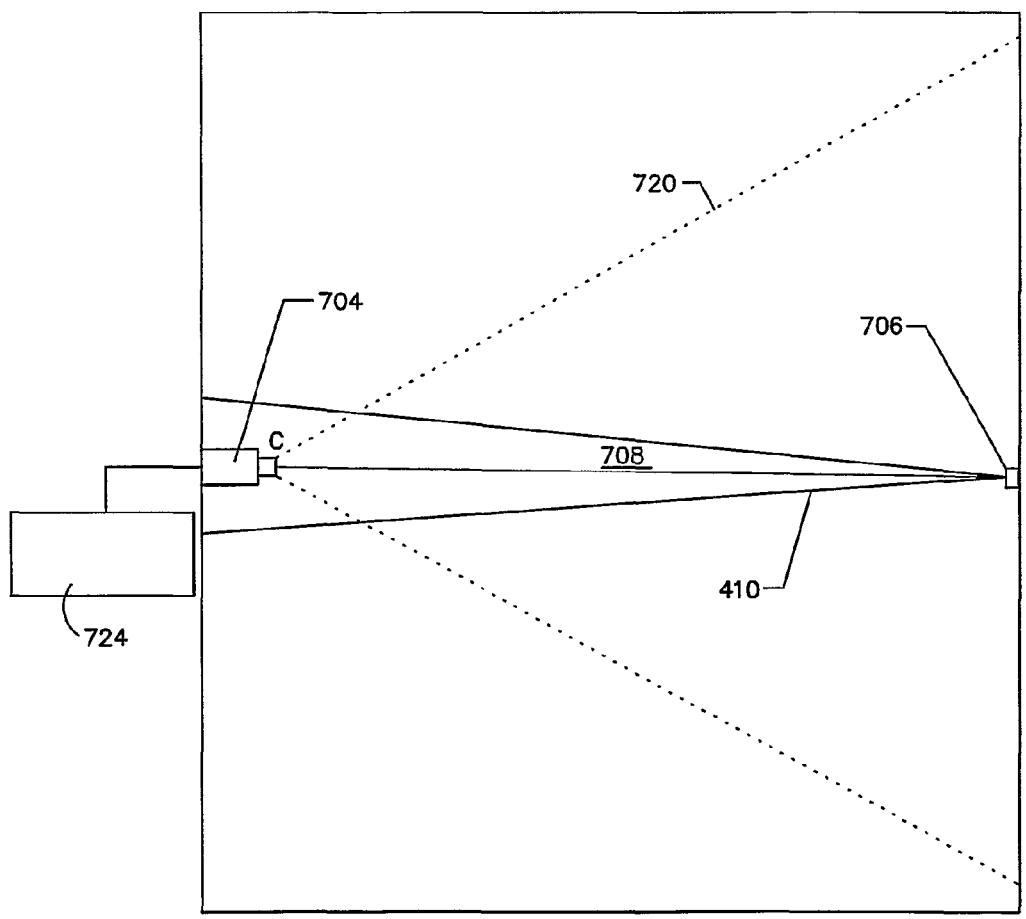
FIG. 7 illustrates a further embodiment of the present invention which does not include a target.

FIG. 7 illustrates yet another embodiment of the present invention. In this example the system 700 includes only a receiver 704 and a light emitter 706 placed on opposing sides of the monitored area 708. In this case the light emitter 706 is the light source imaged by the receiver. Most preferably the light emitter is a battery powered unit, including one or more LEDs or other light emitting elements which are adapted to emit one or more beam of light across the monitored area 708, although other light sources (e.g. powered by mains power, or connected to the receiver by a data cable) could be used. The light emitter 706 is positioned within the field of view of the receiver 704 and is adapted to emit a broad beam (or cone) of light in a volume that includes the receiver 704. The receiver 704 is adapted to process received light (at one or more wavelengths) in the same manner as described above. In this case the microcontroller is adapted to identify those pixels of the image sensor on which light emitted from the light source directly impinges. Particle detection based on the measured obscuration of the received beam then proceeds as described in connection with the previous embodiments. As will be appreciated, the light source can emit light at multiple wavelengths (e.g. by including multiple LEDs or multicolour LEDs or a broad band light source).

In the preferred embodiment the remote light sources are independent of each other and free-running i.e. operate independently of the light receiver (that is, there are no wires or optical communications channels for communication between the receiver and light source(s)). In this embodiment the receiver needs to identify the timing of each light source. It can then go into a process of altering and synchronising its own frame rate with the light sources. This synchronisation will need to be performed for each light source independently and the frame rate continuously adjusted to allow phase synchronisation with each light source in turn.

In a more complicated embodiment the camera could communicate with the remote light source(s) to synchronise the camera frame rate with the illumination modulation of the light sources.

A preferred synchronisation scheme operates as follows. Initially the beacons are turned on and generate light beams according to their modulation scheme at an unknown rate. The receiver is configured to operate continuously and identify the pixel or group pixels of on the image sensor corresponding to each light source. Once this is performed, the receiver can identify the modulation rate of each light source, and adjust either or both of the phase and frame rate of the shutter of the receiver accordingly.

In embodiments of the invention described below, which use a scanning camera or light source, the frame rate and phase of the receiver, and also the modulation rate of the light sources, can be determined to match the scanning rate of the system.

In a preferred embodiment of the present invention, the system will be powered, from the fire alarm loop, thus minimising the installation cost. This minimises the installation costs of the device in that it obviates the need for dedicated wiring for supplying power or data communication between the emitters and receiver. However, the fire alarm loop usually only provides a very small amount of DC electrical power for the detector. For example, an average power consumption of about 50 mW may be desirable for such a detector. However with current technology the power consumed during video capture and processing will be far above the 50 mW that is available from the loop. To address this problem a separate power supply could be used, but this is costly since standards for fire safety equipment are onerous, e.g. they require a fully approved and supervised battery backed supply, and fixed mains wiring.

In order to reduce power consumption at the receiver end it is possible to remotely mount the light sources from the receiver and power the light sources using a battery. This is made possible by using a low power light source such as a LED. Most preferably the light source is modulated with a relatively low duty cycle to extend battery life.

A noted above, when a remotely mounted light source is used there is no need for a reflective target as the remote light source directly illuminates the receiver. However, it can be advantageous to use a hybrid system in which a primary light source is mounted remotely from the receiver, and transmits a beam of light back towards the receiver across the region being monitored, and a second light source is mounted on the receiver. Using such an arrangement, an initial, primary smoke detection can be performed using the remotely mounted light source however, when a predetermined smoke detection threshold (e.g. an obscuration threshold) is reached the receiver mounted light source(s) can be activated. In such a scheme a reflective target will be needed to reflect the beam of the receiver mounted light source back to the receiver for detection. In such a system the receiver-mounted light source can operate at multiple wavelengths to implement multiple wavelength detection as described above. The receiver mounted light sources may operate at the same or different wavelengths to the light sources mounted on the beacon.

Figure 14:
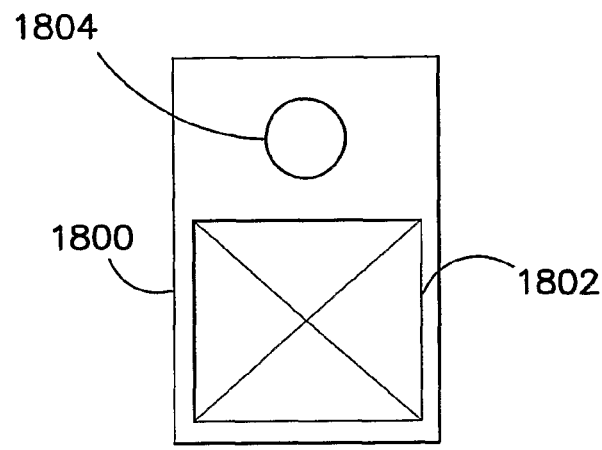
FIG. 14 illustrates a beacon used in an embodiment of the present invention.
Figure 15:
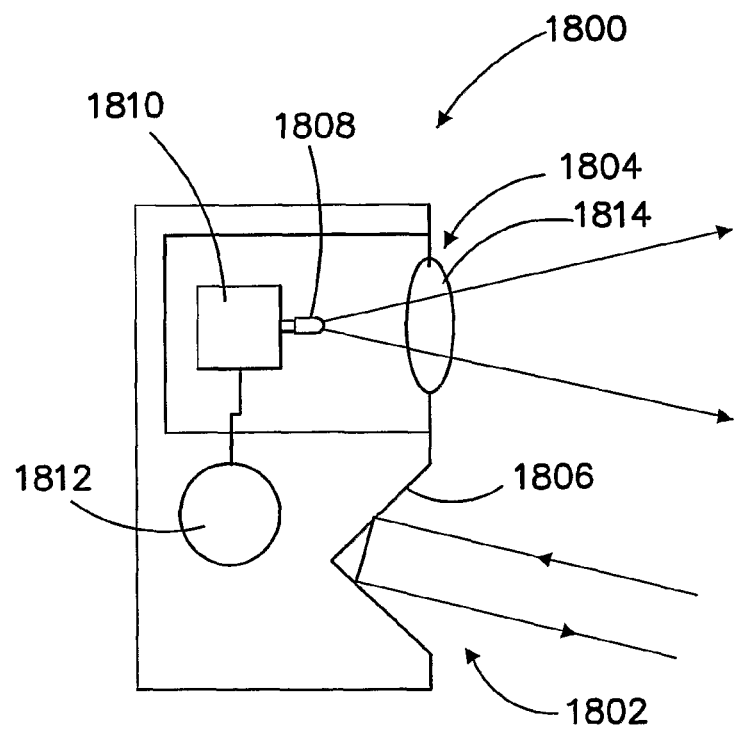
FIG. 15 shows a schematic view of the beacon of FIG. 14.

FIG. 14 illustrates an exemplary combined light source and target arrangement. The beacon 1800 includes a retroreflective target portion 1802 and a light source 1804. FIG. 15 illustrates schematically a cut away side view of the beacon 1800 to better illustrate its construction. The lower half of the beacon 1800 includes a retroreflector, in the form of a corner cube 1806. As will be known to those skilled in the art a corner cube typically includes one or more reflective arrangements having adjacent faces meeting at an internal angle of 90°. Using such an arrangement, light is reflected away from the reflector in a direction parallel to the incoming beam. The top part of the beacon 1800 includes a light source 1804. The light source 1804 is illuminated using an LED 1808 which is connected to drive circuitry 1810 that is powered by battery 1812. The light emitted by the LED 1808 can be passed through an optical system, indicated as lens 1814. As can be seen a device of this type need not be connected to any external power source or linked via a communications line back to the receiver.

In some instances the lens or window of a transmitter or receiver may become obscured due to deposition of water molecules as a condensate on the surface of lens or window.

There are a range of possible approaches to avoid obscuration of the lens in this way. Using FIG. 15 as an example, in one embodiment a heating device is provided within, or proximate to the lens 1814. The heating device operates to increase the temperature of the lens and air within the housing 1814 and assists in reducing obscuration due to condensation. In alternative embodiments, a desiccant or other hygroscopic substance is provided within the beacon 1800 to absorb moisture from the air and thus reduce the likelihood of condensation. As a person skilled in the art would appreciate, either approach is applicable with certain modifications to the receiver 704.

Figure 16:
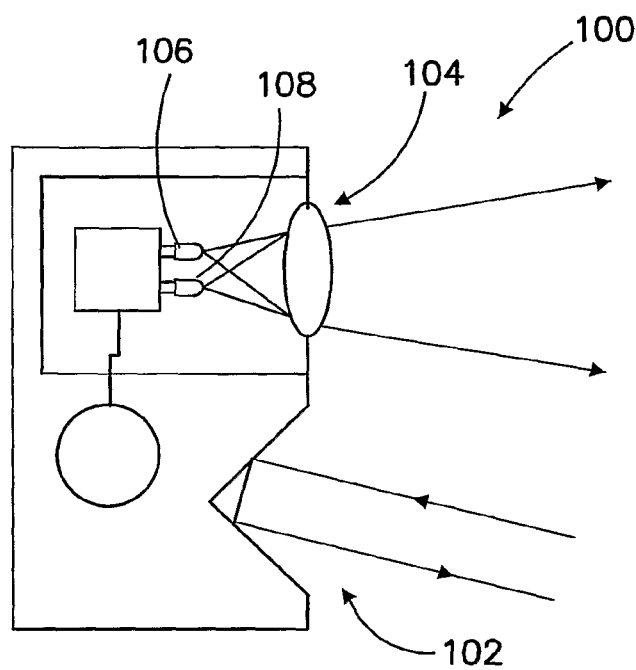
FIG. 16 shows a schematic side view of the variant of the beacon of FIG. 14.

FIG. 16 illustrates a further embodiment of the beacon 100 in accordance with an embodiment of the invention.

In this embodiment the beacon 100 includes a retroreflective portion 102 and a light source portion 104. However, this embodiment differs from that of FIGS. 14 and 15 in that two LED's 106 and 108 are provided. Each of the LED's 106 and 108 can generate a light beam at a different wavelength to enable the particle detector to be operated at multiple wavelengths in the manner described above.

Such a beacon can be used in an embodiment of the present invention employing more than two wavelengths of light for particle detection.

Figure 17:
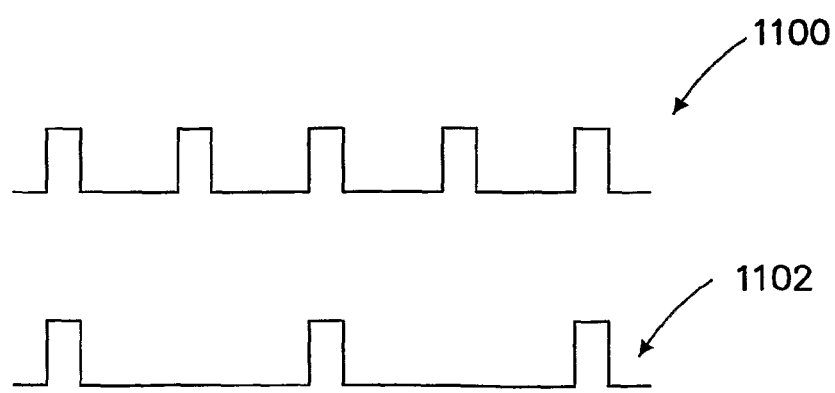
FIG. 17 shows two encoding schemes able to be used by a beacon in an embodiment of the present invention.
Figure 28:
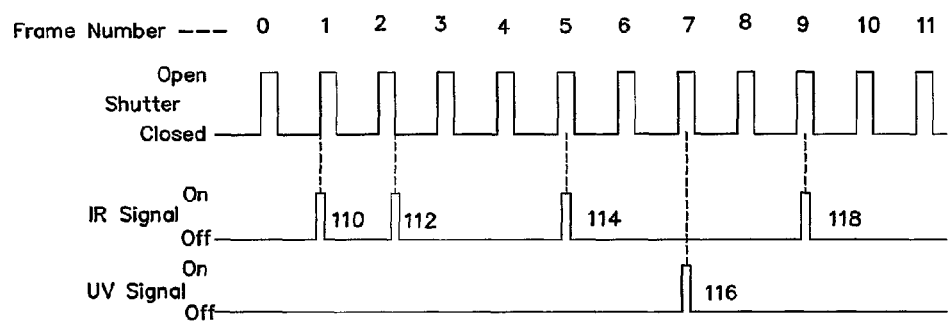
FIG. 28 illustrates an exemplary pulse train used in an embodiment of the present invention.

Because the beacons 1800 and 100 are not connected to an external power source or the receiver via the communications line the illumination of the LED's will typically be modulated such that the LEDs blink from time to time to intermittently emit a beam of light across the region being monitored. FIGS. 17 and 28 show modulation schemes suitable for use in an embodiment of the present invention. Using such a modulation scheme battery life of the remotely mounted beacon can be extended and regular monitoring of particle density in the space being monitored can be performed.

Because the beacons 1800 and 1000 are battery powered, it is necessary to monitor the power remaining in the battery of the beacon. In order to automatically perform this task the beacon can be programmed to change its illumination modulation when a lower battery state is reached. For example, instead of using a modulation scheme 1100, an alternative modulation scheme e.g. scheme 1102 can be employed once the battery voltage drops below a predetermined level. The receiver can be programmed to identify a change in the modulation pattern of the beacon requires new batteries to be installed.

The modulation scheme of the beacon can be switched temporarily or intermittently to the "low battery" modulation scheme 1102 to allow the system to continue operating with full detection capacity. Alternatively, the low battery modulation scheme can be maintained. Whilst this scheme reduces the duty cycle of the LED to prolong battery life further it also halves the number of particle detection readings that are able to be made in the given time period. However, even at this reduced duty cycle it may still be possible to adequately detect particles in the region being monitored.

Figure 18:
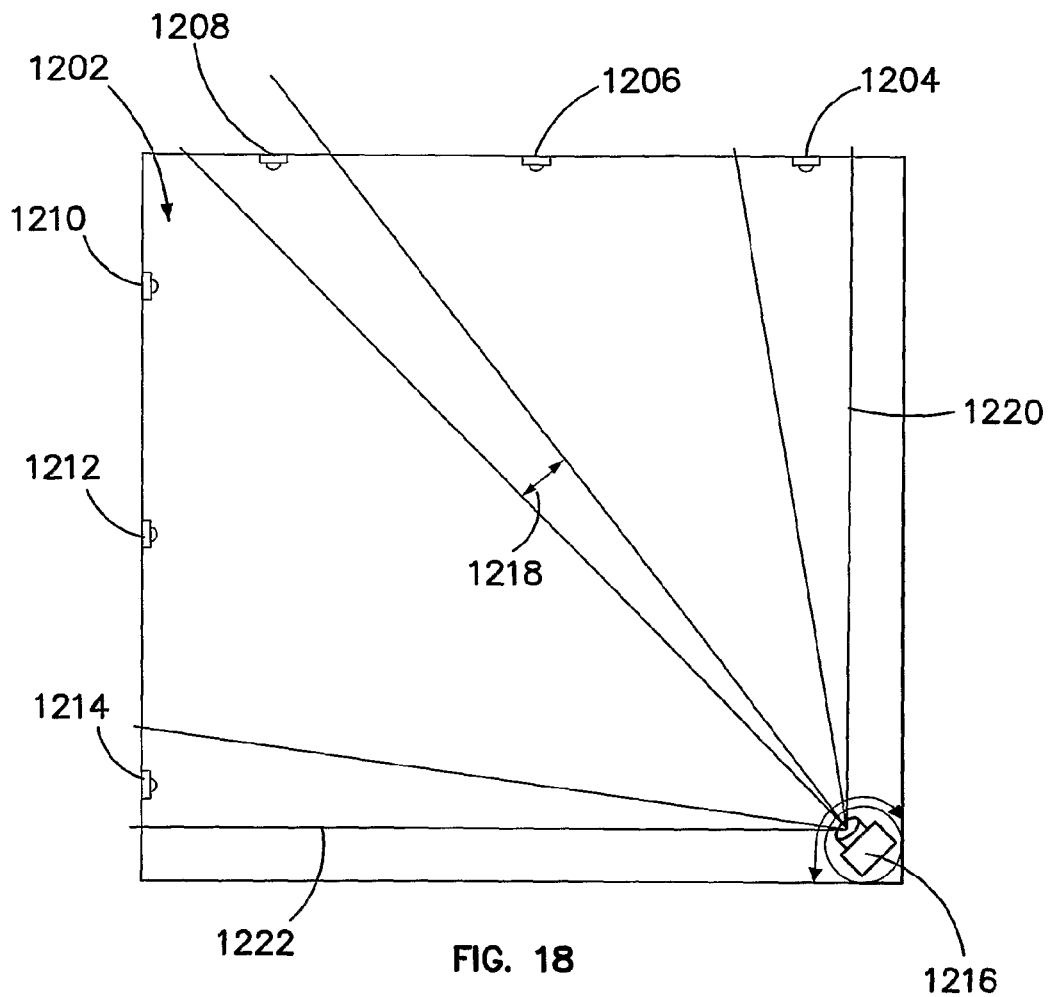
FIG. 18 illustrates a particle detection system according to a further embodiment of the present invention, which uses plurality stationary beacons and a scanning detector to cover a 90° field of view.

In some implementations of the present invention in which the region to be monitored greatly exceeds the field of view of the receiver it is possible to implement a scanning receiver system. FIG. 18 illustrates such a system. In this example, a region to be monitored 1202 has a plurality of beacons 1204 to 1214 arranged around its perimeter. In one corner of the room a receiver 1216 is mounted. The receiver 1216 has a field of view defined by sector 1218. The sector 1218 is relatively narrow and does not encompass the entire region to be monitored and is insufficient to simultaneously view all of the beacons 1204 to 1214. In order to overcome this short coming, the mounting means of the receiver 1216 is configured to scan the receiver's field of view from one side of the room to the other through 90°. For example, the receiver can be panned from a position 1220 in which it can view beacon 1204 to a position 1222 in which it can view beacon 1214. Such a system can be adapted to cover different geometries, e.g. by centrally mounting the camera and rotating it through 360° to view transmitters mounted on all walls of the building. In a further alternative, a centrally mounted static receiver with 360° field of view could be used instead of a rotating element.

The detection software of the receiver is synchronised with the scanning to determine which of the beacons 1204 to 1214 falls within its field of view at any given time, when using a beacon of the type illustrated in FIG. 14 or 16 or a remotely mounted target. Alternatively, a receiver mounted light source with a relatively narrow field of view can also be scanned across the region being monitored in synchronisation with the receiver.

Figure 19:
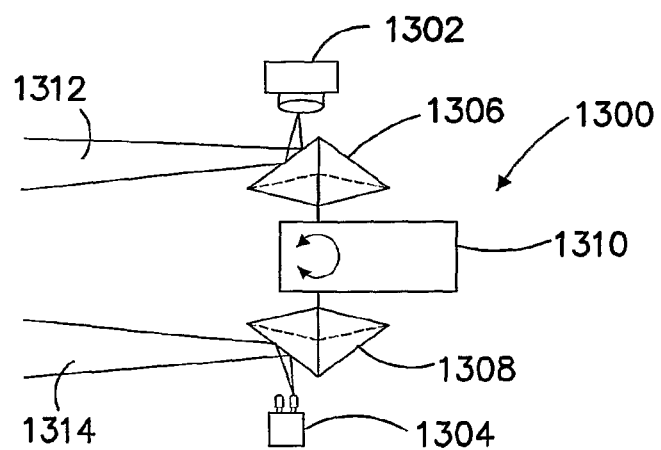
FIG. 19 is a schematic representation of the mechanical system used in a scanning receiver and light source arrangement of an embodiment of the present invention.

FIG. 19 illustrates an exemplary mechanism for scanning both field of view of a receiver and the beam of a light source. The mounting mechanism 1300 includes a receiver 1302 and light source 1304. A pair of rotating mirrors 1306 and 1308 are mounted between them and driven by a drive mechanism 1310.

The rotating mirrors in this example are shaped as a square pyramid and rotate synchronously with each other. The receiver 1304 views a face of the rotating mirror and, as the mirror rotates, the field of view 1312 of the receiver 1302 sweeps through 90° repeatedly. The light source 1304 is similarly mounted with respect to the mirror 1308 and as it rotates, the field of illumination 1314 of the light source 1304 also sweeps through 90°. Because the mirrors 1306 and 1308 are accurately aligned with each other the field of illumination 1314 and the field of view 1312 coincide at the point of the reflective target and are swept together. As will be appreciated by those skilled in the art, the angles swept out by the mechanism of FIG. 19 can be adjusted by changing the number of faces on the mirrors 1306 and 1308. Moreover, in a preferred embodiment the rate of rotation of the mirrors 1306 and 1308 can be controlled to enable synchronisation with the frame rate of the receiver 1302 if desired.

Figure 20:
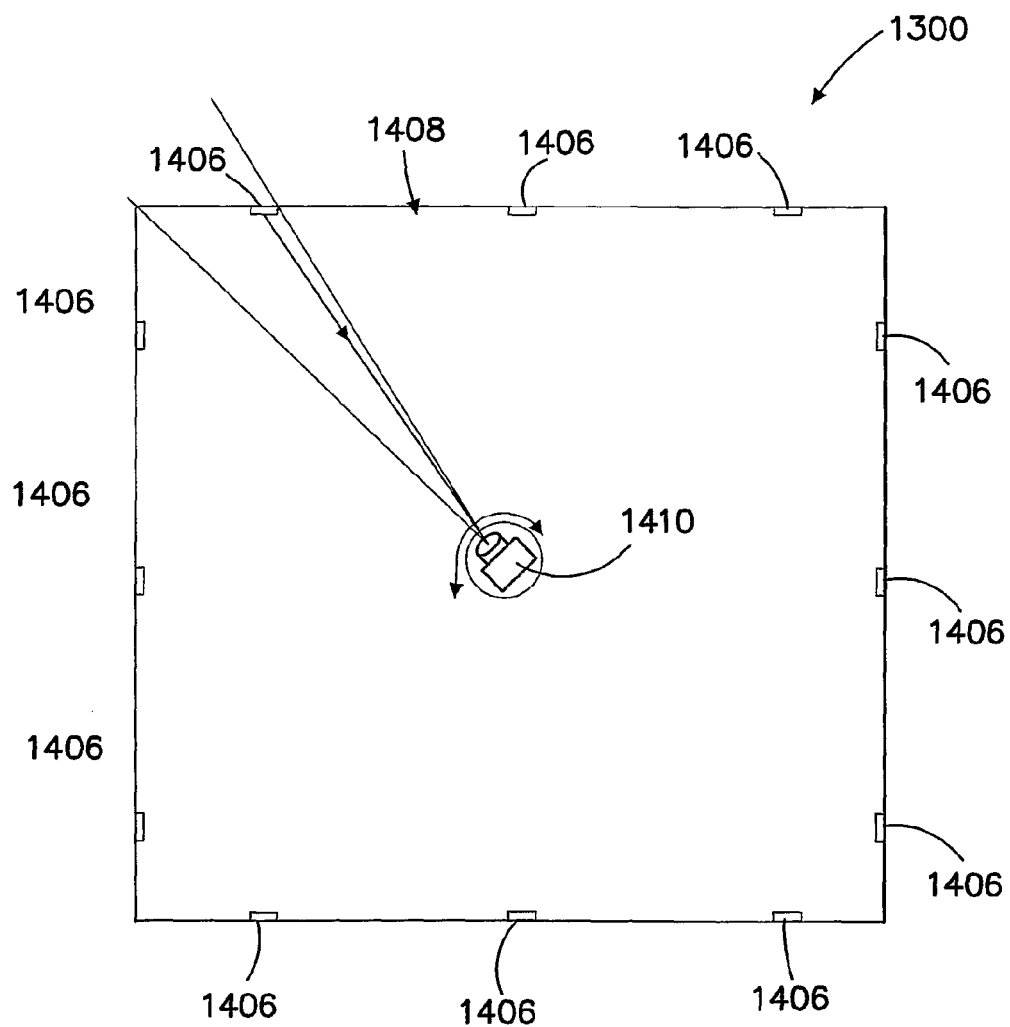
FIG. 20 illustrates a particle detection system according to a further embodiment of the present invention, which uses a scanning camera and light source arrangement to cover a 360° field of view.

FIG. 20 illustrates a further embodiment of the present invention in which a centrally mounted camera and light emitter arrangement are used to detect particles in a region 1408. The camera and light emitter arrangement 1410 is preferably mounted to the ceiling of the room being monitored 1408 and is adapted to sweep a full 360° around the room. The field of illumination of the receiver-mounted light sources coincides with the field of view of the receiver. As the receiver and light emitter arrangement 1410 sweep around the room the plurality of reflective targets 1406 are sequentially illuminated. In effect the particle detection system 1400 operates as a series of radial beam detectors centred at the middle of the room which are sequentially operated to detect smoke around the room. Of course light emitters could be used in place of reflective targets 1406, in which case the arrangement 1410 need not carry a light emitter.

In embodiments of the present invention which use a remotely mounted beacon it can be advantageous to have the light source mounted on the beacon emit a relatively narrow beam of radiation. The use of a narrow beam of radiation increases the intensity of the radiation within the beam for a given level of power use which increases the signal received at the receiver. However, the use of a narrow beam light emitter increases the need for alignment of the light source and the receiver. It should be noted however that a preferred beam divergence of between 5° and 10° is permissible and accordingly that alignment below this tolerance is not needed.

Figure 21:
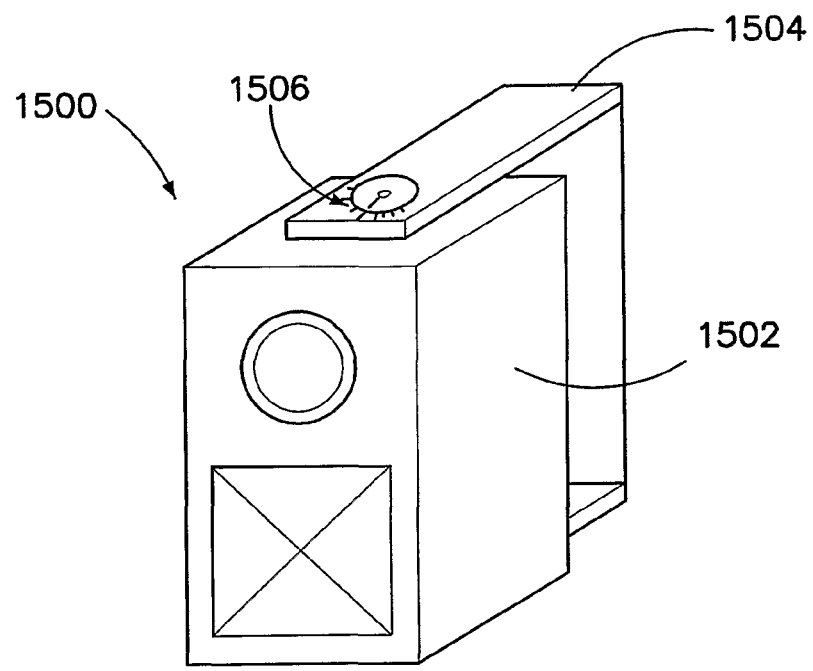
FIG. 21 illustrates a beacon according to an embodiment of the present invention with an alignment mechanism.
Figure 22:
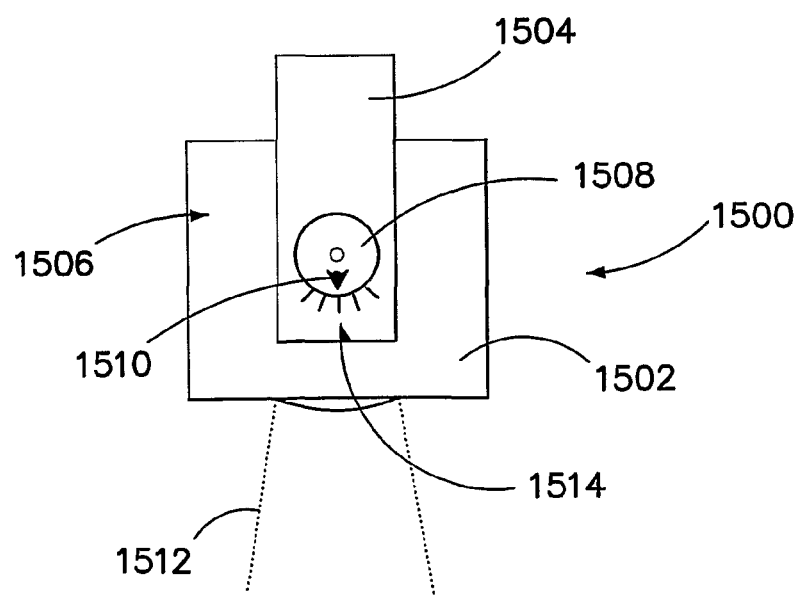
FIG. 22 shows the top view of the beacon of FIG. 21.

In order to facilitate alignment of the light source with the receiver, the inventors have proposed several alignment mechanisms. FIG. 21 illustrates a beacon 1500 including a first alignment mechanism according to an embodiment of the present invention. The beacon 1500 includes a beacon housing 1502 and is mounted on a bracket 1504. The beacon housing 1502 is rotatable with respect to the bracket 1504 to allow alignment of the receiver with respect to the bracket. In this embodiment, the beacon 1500 is provided with an indicator dial 1506 to assist with alignment during installation. A close-up of the top of the beacon 1500 in shown in FIG. 22 and better illustrates the operation of the indicator dial 1506. The indicator dial 1506 includes a central portion 1508 which is in a fixed angular relationship with respect to the housing of the beacon 1502 and includes an indicator arrow 1510 which is aligned with the centre line of the field of illumination 1512 of the light source housed within the beacon. The indicator dial 1506 additionally includes a series of angular graduated markings 1514 which indicate an angular position with respect to the mounting plane of the bracket 1504.

Typically the geometry of a smoke detection system installation according to an embodiment of the present invention will be known before final installation takes place. Accordingly, the orientation and position of a beacon with respect to the receiver should be known. In this case, the installer can simply calculate the appropriate angle at which to set the beacon with respect to its mounting bracket and simply align the beacon with respect to the bracket such that the arrow 510 on the dial aligns with the appropriate marking 1514 on the dial face.

Figure 23:
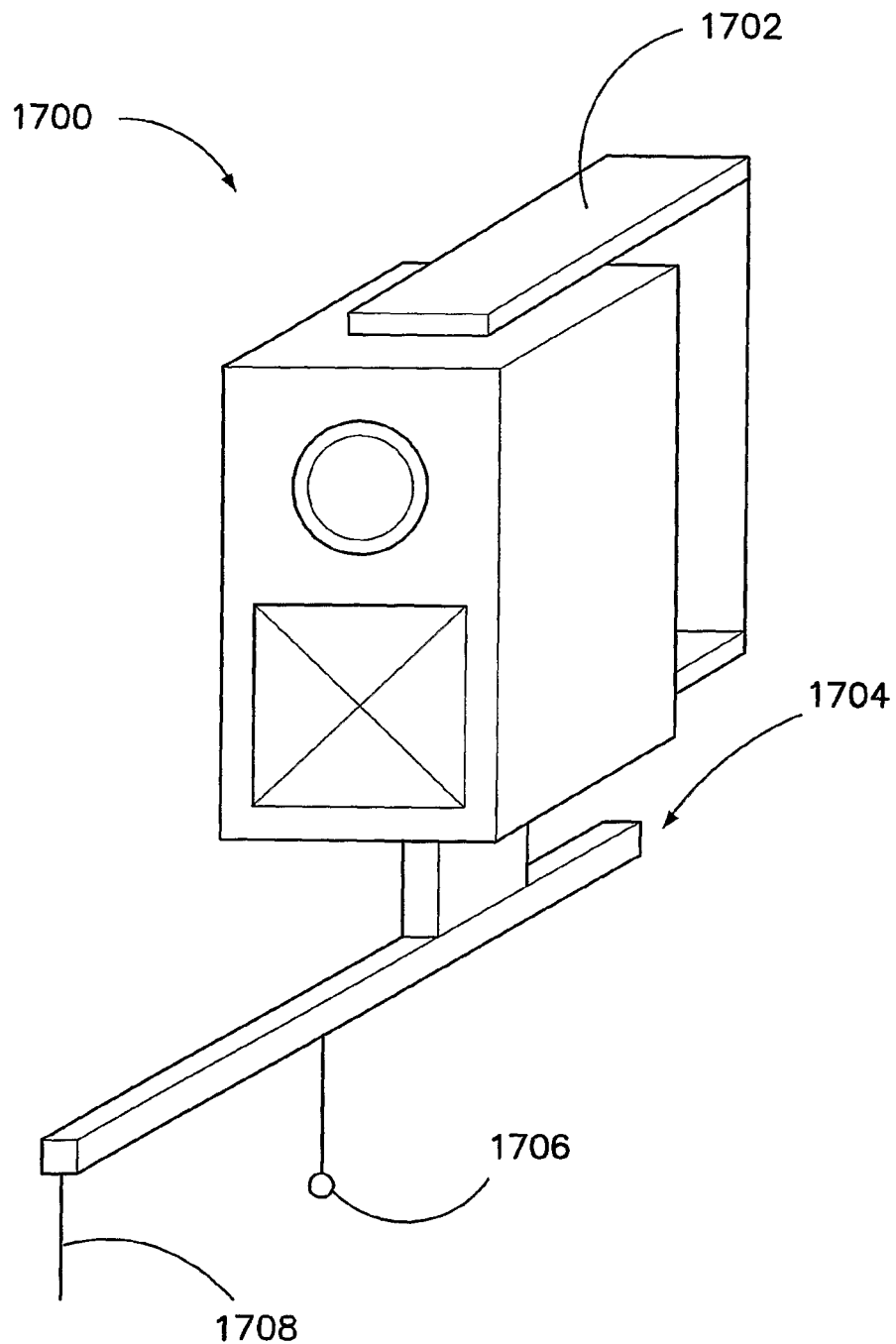
FIG. 23 shows another means for aligning a beacon in an embodiment of the present invention.
Figure 24:
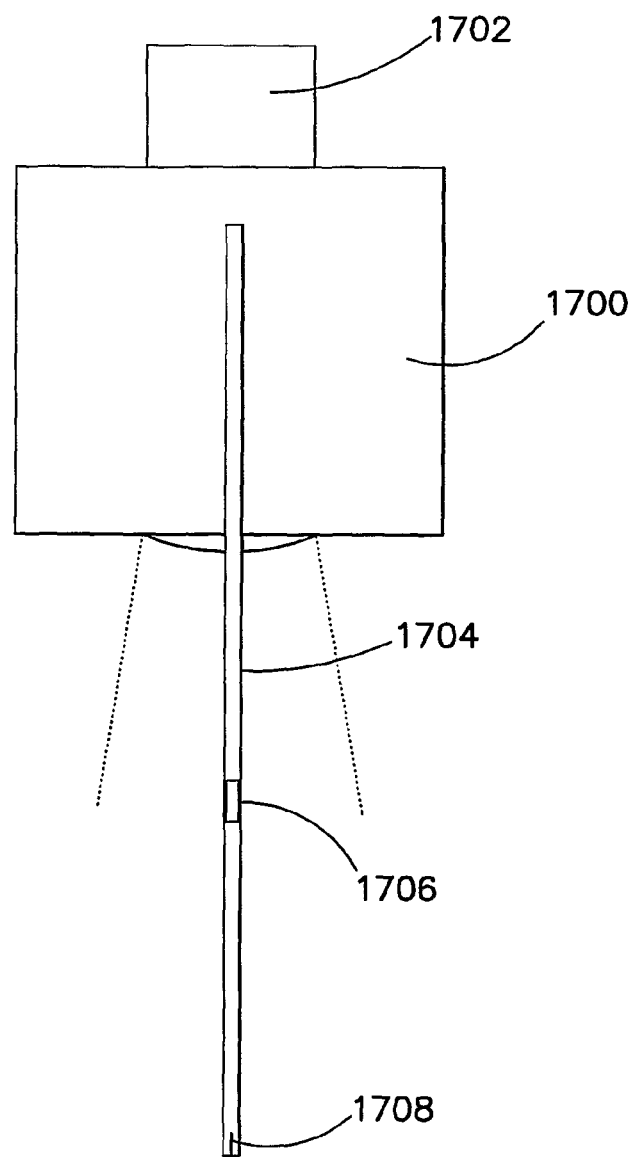
FIG. 24 shows a bottom view of the alignment means of FIG. 23.

FIGS. 23 and 24 illustrate a further alignment mechanism usable in an embodiment of the present invention. In this embodiment the beacon 1700 is mounted on a mounting bracket 1702 in a manner that allows it to swivel about its point of attachment. The alignment of the beacon 1700 can be determined by attaching a removable sight mechanism 1704 to the beacon 1700. The sight mechanism 1704 operates similar to a gun sight and includes a viewing means such as eye piece 1706 and a site marker 1708. In use, after mounting the bracket 1702 to its support surface the installer can change the angle orientation of the beacon 1700 by pivoting it in the bracket such that the receiver is aligned with the sight attached to the beacon. After installation the sight can be detached from the beacon and used to align other beacons which form part of the smoke detection system.

Figure 25:
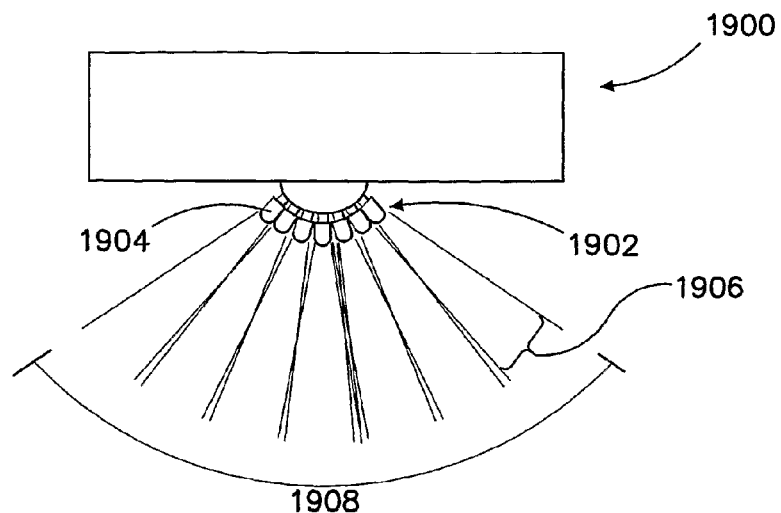
FIG. 25 shows a beacon according to a further embodiment of the present invention.
Figure 25A:
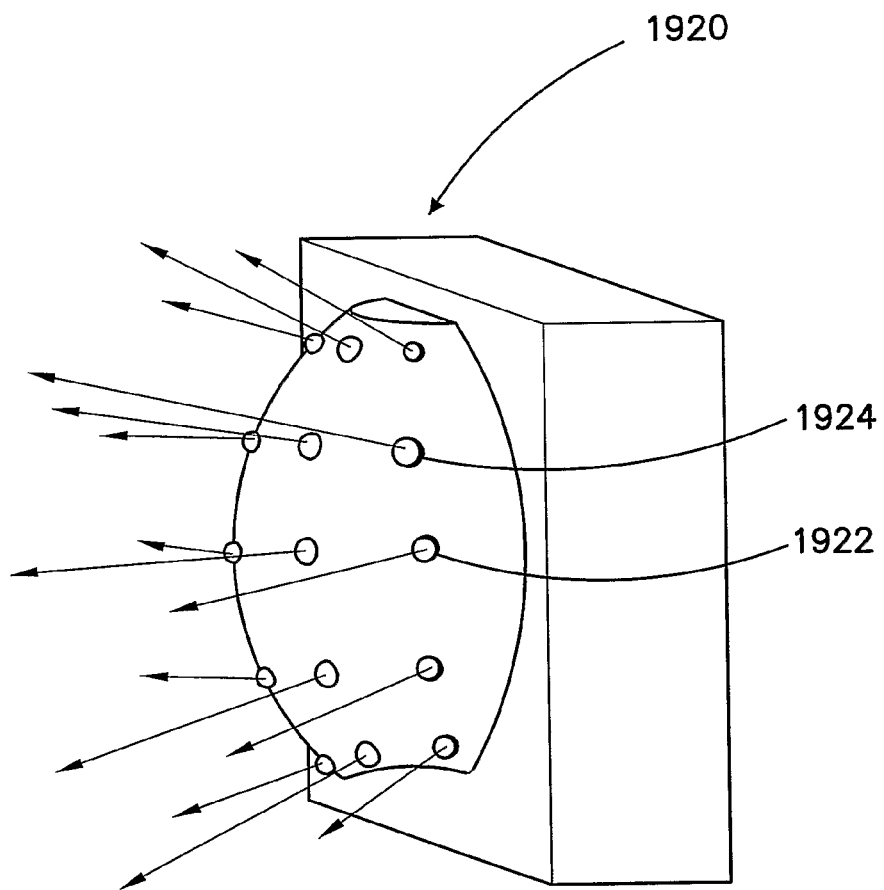
FIG. 25A shows a beacon according to a further embodiment of the present invention.

FIGS. 25 and 25A illustrate an alternative beacon arrangement which can be used in an embodiment of the present invention. For clarity a light source portion of a beacon 1900 is illustrated. However, the beacon may include a retroreflective portion as indicated in previous embodiments.

In this beacon 1900 the light source is formed by a plurality of light emitters, for example LEDs 1902,1904. Each of the light emitters produces a beam of light, such as beam of light 1906 produced by the light source 1902, which has a relatively narrow dispersion pattern. Preferably, the illumination produced by neighbouring light sources overlap to enable illumination over a wide field of illumination as indicated at 1908. In use, once the beacon 1900 is mounted to a surface the individual light emitter which is best aligned with the receiver can be used to form a light beam directed toward that receiver. In a system in which multiple receivers are used to monitor the beacon 1900 two or more of the individual light emitters 1902,1904 can be illuminated to define the separate beams directed to the individual receivers.

Upon set up of the system the operator can manually select the individual light emitter which is most closely aligned with the receiver or an automatic light source selection algorithm can be employed. For example, initially all light sources can be turned on such that the beacon can be identified within the field of view of the receiver and then the light sources can be sequentially turned off (or on again) in a pattern to identify which of the individual light sources 1902 or 1904 best illuminates the receiver.

The light source may be configured to illuminate beams over various spatial patterns. For example, FIGS. 25 and 25A show emitters having a semi-circular profile, with each emitter being positioned on a point on a circumference of a semicircle. However, other configurations are possible. For example, further light sources may be added such that the light source extends both vertically and horizontally to different extents. In the embodiment of FIG. 25A, light emitters are arranged hemispherically in this way, a beacon can be chosen with an additional degree of freedom when compared to a linear/planar arrangement. Other embodiments are possible including arrangements of light emitters in other geometric shapes, surfaces or volumes.

Figure 26:
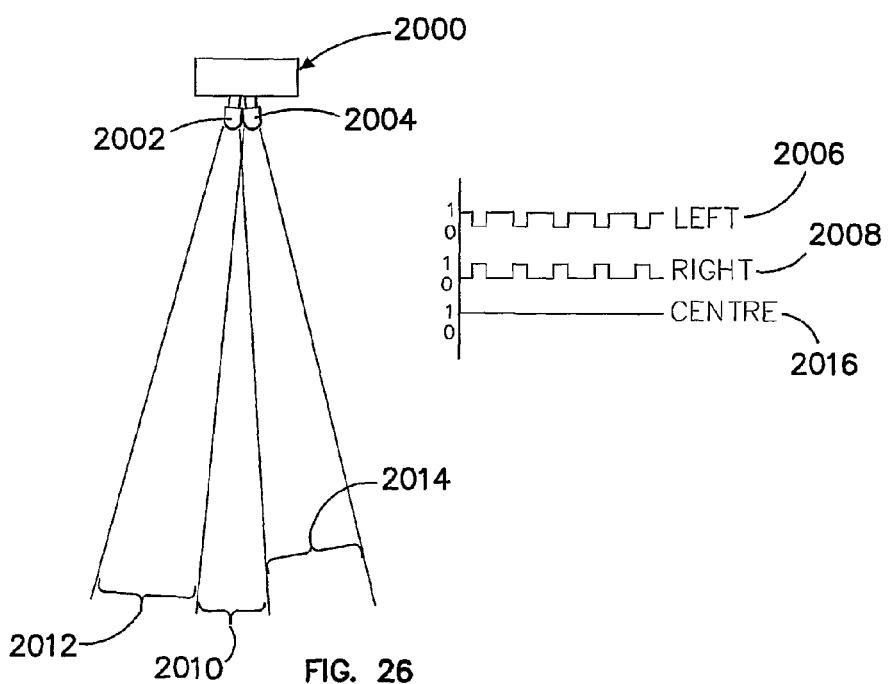
FIG. 26 illustrates a further beacon usable in another embodiment of the present inventions.

FIG. 26 illustrates another type of beacon which can be employed in the embodiment of the present invention. In this case the beacon 2000 includes two individual light sources 2002 and 2004 which transmit light at different wavelengths. During a set up phase the first light source 2002 can be turned on and off with a modulation scheme indicated at 2006 and the light source 2004 can be illuminated with a modulation scheme 2008.

Because it is necessary for the receiver to receive light from both light sources at the same time it is necessary for the receiver to be in the field of illumination of both light sources 2002 and 2004, that is the receiver must be aligned within region 2010. During set up, it is possible to use the receiver to determine whether the beacon is correctly aligned with the receiver in the following manner. Firstly, the light sources 2002 and 2004 are illuminated with the modulation patterns indicated at 2006 and 2008. If the beacon 2000 is correctly aligned with the receiver the receiver will lie in the region 2010. Because the modulation schemes 2006 and 2008 are shaped in a complementary fashion i.e. when one is on the other is off, and they are distinguishable from each other by their modulation patterns, the receiver should receive a constant "on signal" when it is correctly aligned. On the other hand, if the beacon is aligned such that the receiver lies in region 2012 the pattern of received light will resemble the modulation scheme 2006. If the received light appears to be modulated with the pattern as indicated by modulation pattern 2008 the receiver lies within the region 2014.

Thus the system is able to tell the installer whether the beacon 2000 is correctly aligned with the receiver, and if it is not it can tell the operator in which direction the beacon should be adjusted to correctly align the beacon with the receiver.

As will be appreciated with the embodiments of FIGS. 25 and 26 a linear arrangement of light emitters is illustrated. However the array of light sources 1902,1904,2002,2004 can be expanded in two dimensions to allow correct alignment to be achieved in the vertical and horizontal planes as illustrated in FIG. 25A. FIG. 25A shows a beacon 1920 including LEDs 1922, 1924 projecting beams which diverge from each other in two dimensions.

Returning now to FIG. 8, which shows a particle detector according to an embodiment of the present invention which has been extended to include six beam detectors. The system 800 is configured to monitor a space 801 using a single receiver 802 to monitor six targets 804, 806, 808, 810, 812 and 814. Light is emitted from a receiver mounted light source (not shown). The light source emits light over a 90° sector illuminating the entire space between the lines 816. The receiver 802 also has a similarly wide field of view, which covers approximately 90°.

The reflected light from each of the targets 804 to 814 defines six beams 818, 820, 822, 824, 826 and 828. Each of beams 818 to 828 is directed back to the receiver 802 by a respective one of the targets 804 to 814. As described above, each of these beams will form an image on a different pixel or group of pixels on the image sensor of the receiver 802 and can thereby define independent beam detectors. By providing an array of beam detectors radiating out from a corner of the space 801 the entire room can be monitored. Moreover, since each of the beam detectors operates effectively independently from each other a measure of addressability can be achieved. For example, consider a small, localised smoke plume 830 which forms in a part of the room. Initially, this smoke plume 830 will not necessarily intersect with a beam of the beam detector however, as it spreads to form smoke plume 832 it will intersect with beam 820 and the beam detector formed by the light source, reflector 806 and light sensor 802 will detect this smoke plume. Thus it can be determined that smoke is being detected somewhere along the line of beam 820. In the event that the plume spreads further, say to form smoke plume 834, the plume 834 will additionally intersect the beam 818 and the smoke detector formed by the light source, reflector 804 and light receiver 802 will also detect smoke. This can indicate that firstly the smoke plume has increased in size, and secondly that the smoke plume (or smoke plumes) have occurred somewhere along the lines of beams 820 and 818.

As will be appreciated by those skilled in the art, each of the beam detectors can have independent alarm logic and be independently identified on the fire alarm loop and be configured to separately trigger an alarm.

Figure 8:
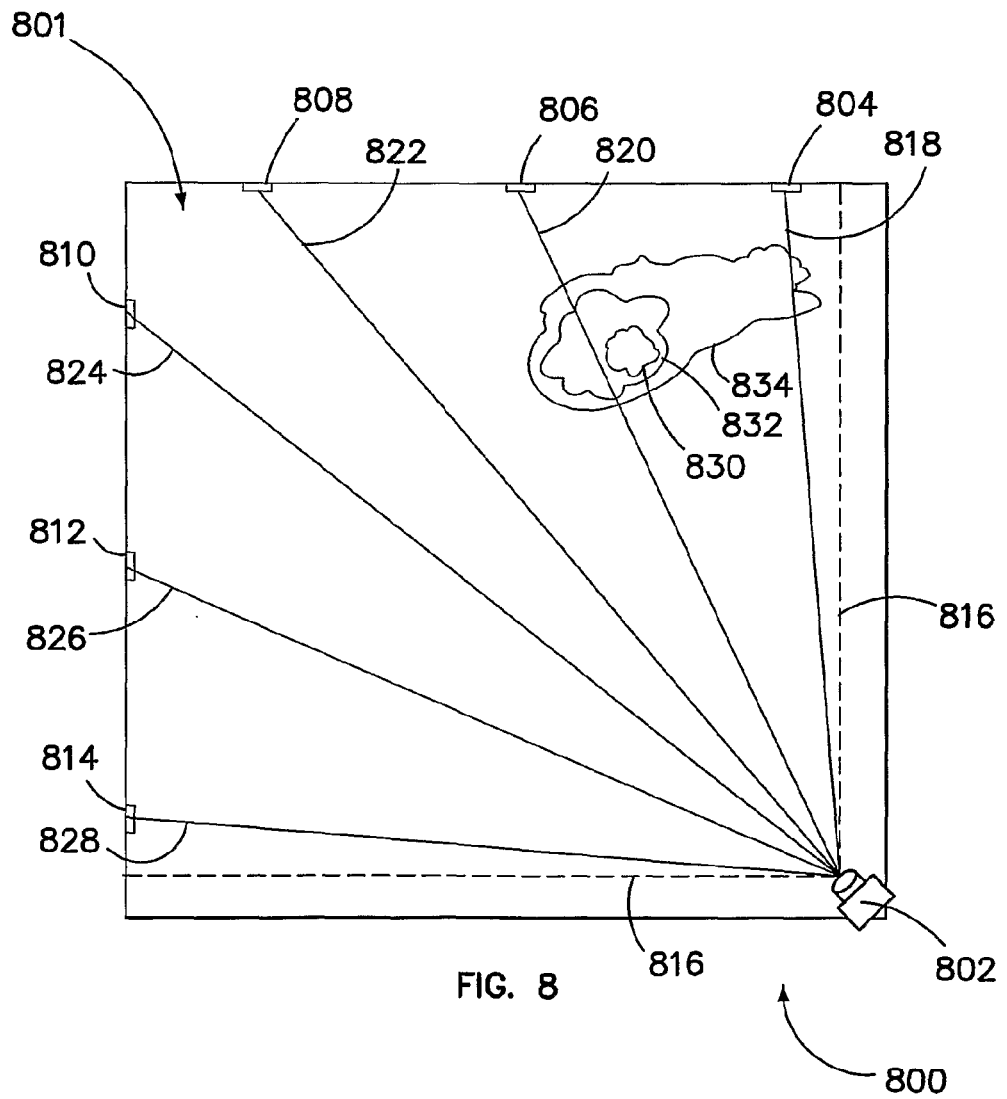
FIG. 8 illustrates a further embodiment of the present invention having six light beams spanning a monitored area.
Figure 9:
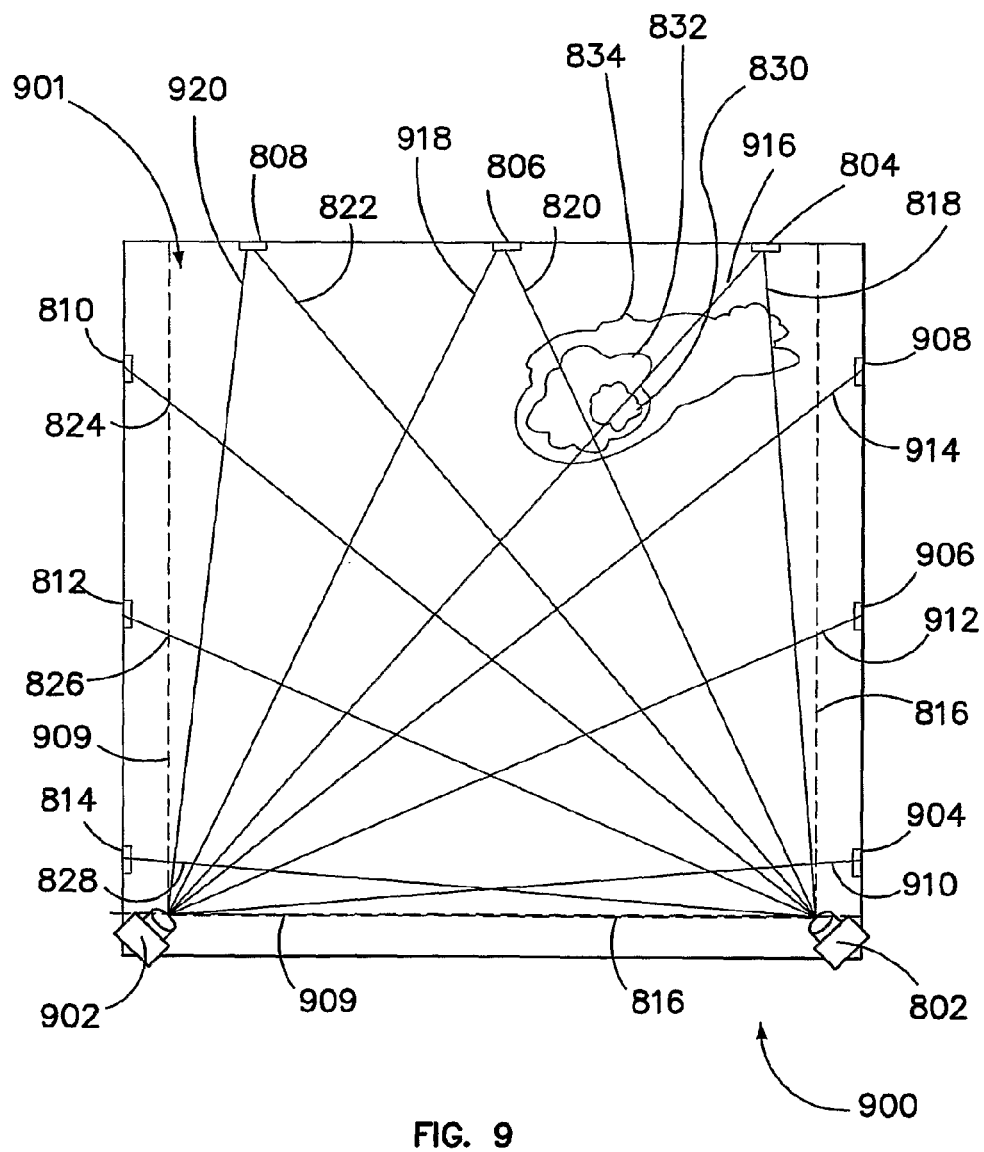
FIG. 9 illustrates a particle detection system illustrating an addressing scheme according to a further aspect of the present invention.

FIG. 9 illustrates a system 900 which provides enhanced addressability. The system 900 includes each of the components of the system of FIG. 8 and also includes an additional receiver (and associated light sources) 902. The system 900 also includes three additional reflective targets 904, 906 and 908. The field of view of the receiver 902 is defined by lines 909 and substantially covers the entire space 901. Thus, the receiver 902 can see six reflectors 904, 906, 908, 804, 806 and 808 in its field of view. Accordingly, the receiver 902, its light sources and its viewable reflectors form six beam detectors defined by beams 910, 912, 914, 916, 918 and 920. As can be seen, these beam detectors intersect with the beams received by the light receiver 902.

By providing intersecting beam detectors the addressability throughout the monitored area 901 is greatly enhanced. Take once again, a small smoke plume 830. When it initially forms, it intersects the beam 916 formed by the receiver 902, its light sources and reflector 804. As it increases in size over time to form smoke plume 832 the smoke plume 832 also intersects beam 820 formed by the receiver 802, its light sources, and the reflector 806. Thus, the position of the smoke plume 832 can be localised to the intersection between beams 916 and 820. As the smoke plume increases in size, its growth can be more accurately determined as it additionally intersects with beam 818 and will be detected by the beam detector defined by the receiver 802, its light sources and the reflector 804. However, it should be noted that as it does not intersect any other beam it can be determined that the smoke plume 834 is growing in a particular defined region.

In this embodiment in addition to each beam being independently addressable each intersection point can be nominated as an addressing point on a fire alarm loop or similar system and the correlation between detections on each of the independent beam detectors can be determined in software to output a localised position of smoke detection. In this way, the intersecting beams each act as a virtual point detector detecting smoke at the point of intersection.

It will be appreciated that the embodiment of FIG. 9 enables a great increase in addressability with the addition only of a single receiver and through additional targets over the system of FIG. 8. In this case, 27 unique points can be addressed by the system.

Whilst the description herein has discussed intersecting beams, the beams need not actually intersect, but merely pass nearby each other so that they monitor a substantially common location within the monitored region.

FIG. 10 shows another system 1000 which is able to provide addressability. In this embodiment, the system of FIG. 8 has been augmented with a plurality of additional reflective targets 1002, 1004, 1006, 1008, 1010, 1012 and 1014. The reflective target e.g. 1002 can be the type illustrated in FIG. 10A.

In FIG. 10A the reflective target 1050 includes a retroreflective target surface 1052 mounted on a mounting bracket 1054. The mounting bracket 1054 is preferably adapted to be mounted to ceiling of the space being monitored 1001 such that the reflective surface 1052 of the target 1050 hangs downward and is illuminated by a light source of the detector and is also in the field of view of the receiver.

By placing reflective targets 1002 to 1014 at intermediate positions across the region being monitored 1001, addressability along the length of the beams can be achieved. In this embodiment, the reflectors 1002 to 1012 have been placed close by a corresponding full length beam 818 to 828. Thus a smoke plume which intersects beam 818 is likely to also intersect the beam 1016 which is reflected by reflector 1002 if that smoke plume is positioned between the reflector 1002 and the receiver 802. If the smoke plume occurs further away from the receiver 802 than the reflector 1002 then only the beam detector on beam 818 will detect smoke. Furthermore, pendant reflectors can be placed at other positions, for example midway between other beams e.g. pendant 1014 which reflector beam 1018 midway between beams 818 and 820. As discussed in the previous embodiments a small smoke plume 830 which initially forms and does not intersect any of the beams will not be detected by such a system. However, once it has grown to plume 832 it will intersect the outer part of beam 820 and be detected by the particle detector defined by the receiver 802, its associated light source, reflector 806. However, because it is further away from the receiver than the reflector 1004 it will not intersect beam 1020 and thus will not be detected by the beam detector defined by that reflector. Accordingly, the smoke plume can be determined to be at some portion on the outermost part of beam 820. As the plume further increases in size to form plume 834 it will intersect three beams, namely beam 820, beam 1018 and the outer part of beam 818. Accordingly, it can be determined with high certainty that the smoke plume 834 is forming on the outer parts of beams 818 and 820 and also intersects beam 1018. It can be seen that by placing a plurality of such intermediate reflectors within the field of the receiver 802 addressability of the system can be greatly enhanced. Such an embodiment can be implemented to great effect in an environment which has multiple roof beams across the space being monitored as each roof beam will effectively define a plane on which reflectors may be conveniently mounted and provide depth addressability along the beam. In this embodiment, the light receiver 802 will need to be placed out of the plane defined by the plurality of beams in order to be able to view each of the beams separately. Clearly any of the addressing schemes described herein could be implemented with remotely mounted light emitters rather than reflective targets, as illustrated. Moreover, a combination of the addressing schemes of FIGS. 9 and 10 could also be used.

The present inventors have realised that since smoke detectors do not need to respond instantaneously, acceptable average power consumption could be obtained by activating the video capture and/or video processing subsystems of the smoke detector intermittently, interspersed with periods when processing and capture is suspended. Thus the system can enter a "freeze" state in which it is designed to consume very little or no power. A first way of achieving this solution is to provide the video processing subsystem of the particle detector with a simple timer unit which operates to activate the video capture and processing subsystems intermittently. However, in the preferred form of the system the transmitter 324 is not powered from the loop or other mains power, but is battery powered and is preferably not connected to the receiver 322 or in high speed communication with it. Consequently the transmitter 324 must emit light at only very low duty cycle to conserve power. In such a system the timing of each transmitted burst of light may neither, be controlled by the receiver or synchronised with any other receiver which may also be communicating with the same transmitter 322.

Furthermore, during the video processor "freeze" period the receiver 322 may still be required to manage other functions such as servicing polls from the fire alarm loop, or blinking display LEDs or the like. Therefore, using a simple timer mechanism to activate the video processor and awake it from its "freeze" state is not the preferred solution to this problem.

In a preferred form of the present invention the receiver 322 employs a secondary processor, having much lower power consumption than the video processing processor, or primary processor, which is used to activate the main processor and to deal with other functions that must continue without interruption when the main processor is in its "freeze" state.

Figure 27:
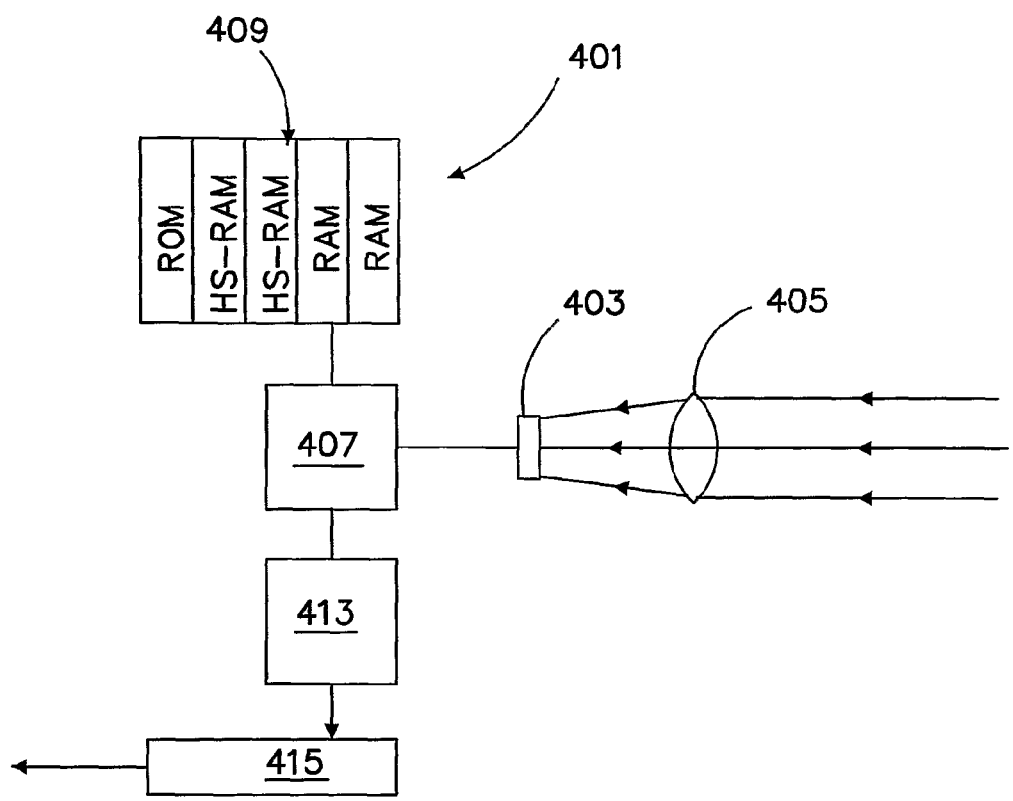
FIG. 27 illustrates a schematic block diagram of a receiver component of beam detector according to an embodiment of the present invention.

FIG. 27 illustrates a schematic block diagram of a receiver 401 embodying the present invention.

The receiver 401 includes an imaging chip 403, e.g., a CMOS sensor manufactured by Aptina Inc, part number MT9V034, for receiving optical signals from a transmitter 324. It may optionally include an optical system 405 e.g. a focusing lens, such as a standard 4.5 mm, f1.4 c-mount lens, for focusing the received electro magnetic radiation onto the imaging chip in the desired manner.

The imaging chip 403 is in data communication with a controller 407 which preferably is an Actel M1AGL600-V2 field programmable gate array (FPGA), and an associated memory 409 including a PC28F256P33 flash ROM for program storage, two IS61LV51216 high-speed RAMs for image storage and two CY621777DV30L RAMs for program execution and data storage. The controller's function is to control the image chip 403 and perform the required sequence of data manipulations to carry out the functions required by the detection system. The control means has sundry additional components as required for correct operation as well understood by those skilled in digital electronics design.

A second processor 413 is also provided. This processor 413 can be a Texas Instruments MSP430F2122 microcontroller or similar, and performs functions such as checking the health of the control means and if needed signaling fault to external monitoring equipment if the control means fails or if the control means, for any other reason, cannot perform its required tasks. It is also responsible for the timely control of power to the control and imaging means in order to minimize power consumption. This is performed by processor 413 de-activating the main processor 407 when it is not needed and waking it up intermittently when it is required.

Processor 413 is also in data communication with interface means 415 such as a display or user interface and is also connected to the fire alarm loop to enable data communication with other equipment connected to the fire alarm loop e.g. a fire panel.

In the preferred embodiment the interface means is used to notify external monitoring equipment if an alarm or fault condition exists. If it is determined by the receiver that a fault exists, the interface means notifies this to the monitoring equipment by opening a switch thereby interrupting the current flow out of the aforementioned monitoring equipment. In the preferred embodiment the switch is a solid state arrangement employing MOSFET transistors which has the benefit of being activated and deactivated with very low power consumption. If it is determined by the receiver that an alarm condition exists, the interface means notifies this to the monitoring equipment by drawing current in excess of a predetermined threshold value from the monitoring equipment. In the preferred embodiment the excess current draw is achieved by the positioning of a bipolar-transistor, current-limited shunt across the interface wires from the monitoring equipment. A total current draw of approximately 50 mA is used to signal the alarm condition. In the preferred embodiment, power for normal operation is drawn from the connecting wires to the monitoring equipment at a constant current of 3 mA under non-alarm conditions.

In the preferred embodiment of the present invention the transmitter 324 includes a controller to control its illumination pattern, controlling the illumination time, sequence and intensity for each of the light sources, e.g. infra-red and ultra-violet. For example this could be a Texas Instruments MSP430F2122 microcontroller. The microcontroller also detects activation of the device when first installed. In the preferred embodiment of the transmitter, the power source is a Lithium Thionyl Chloride battery.

In a preferred form of the present invention, during commissioning of the system the main processor 407 can be programmed to discover the illumination pattern of each of the light sources and over a period of preferably several minutes e.g. 10 minutes, determine its activation pattern. This process can be repeated for all light sources associated with the receiver. The low power processor 413 can use the discovered light source sequencing information to activate processor B at the correct time.

As will be appreciated, by using a system of this structure the function of the system which must operate at all times can be controlled by the very low power consumption processor 413 whilst the highly intensive processing can be performed intermittently by the main video processor 407, and in doing so the average power can be maintained at a relatively low level.

The inventors have determined that, there are various and often competing constraints associated with practical embodiments that must be dealt with when choosing the illumination pattern of the transmitter and corresponding receiver operation to accurately acquire and track a transmitter output. For example, in some systems it is desirable to use the rate of change of attenuation is used to distinguish fault conditions from particulate detection events. This complicates the use of long integration times discussed in the background. The preferred embodiment uses an integration period of 10 seconds for normal measurements, and a shorter integration period of one second is used for rate of change based fault detection.

Another constraint on system performance is the scene lighting level. For a practical system it is usually necessary to assume the scene may be lit by sunlight for at least part of its operational life. There may also be limitations on the ability to use wavelength selective filters on the camera (e.g. at least cost limitations). Therefore, it will be necessary to use short exposures to avoid saturation, and still leave sufficient head room for the signal. In preferred implementations of the system the exposure duration is 100 us, but the optimum value will depend on the choice of sensor, filter, lens, worst case scene lighting and the amount of headroom required for the signal.

A means of synchronising the receiver with the transmitter is also required. It is preferable to achieve this without the use of additional hardware such as a radio system or hard wiring between components. Instead in one desirable implementation the synchronisation is performed optically using the same imaging and processing hardware that is used for particle detection. However, as a person skilled in the art will appreciate, the use of the same hardware for particle detection as for synchronisation links two concerns within the system, and thereby imposes a further constraint on the possible solutions.

Another constraint within the system is due to the presence of noise. The prime noise sources in the system are camera shot noise and noise from light variations in the scene. Dark noise is generally not a significant contribution for systems that must deal with full sunlight. Scene noise is dealt with very effectively by the background subtraction method described in our earlier patent applications. Shot noise cannot be totally removed, as it is fundamental to the quantum detection process. However, shot noise can be reduced by reducing exposure time, and also by summing fewer exposures. In the preferred embodiment, substantially all transmitter power is put into very brief flashes, with a repetition rate that still allows an adequate system response time.

For example, a flash rate of 1 per second will satisfy the response time requirement, and a flash duration of less than 1 μs and an exposure time of 2 μs could (in principle) be used. In practice this would be very difficult to synchronise. In addition, the transmitter LEDs would need to handle a very high peak current to deliver the energy in such a short time, which in turn would increase cost. Another limitation is the dynamic range of the sensor. Putting all the power into one flash per second could result in saturation in the sensor.

In consideration of the above factors the preferred embodiment uses an exposure of 100 μs, a flash duration of 50 μs, and a period of 300 ms. An integration length of 3 samples is used for rate of change based fault detection. An integration length of 30 samples is used for smoke measurements.

To perform the background cancellation techniques, the receiver also needs to capture images just before and just after the flash that are used to eliminate the contribution from the scene. Ideally these "off" exposures would occur as close to the "on" exposure as possible to optimise cancellation in the case of a time varying background. With the receiver system used in the preferred implementation, the maximum practical frame rate is 1000 fps, so the "off" exposures are spaced 1 ms either side of the "on" exposure.

In one form, the transmitter optical output consists of a series of short pulses, with a very low duty cycle. The pulses are placed to match the frame rate of the imaging system (e.g. 1000 fps). FIG. 28 shows an exemplary pulse sequence in relation to the sensor exposures in the receiver. In this case the transmitter is adapted to emit light in an IR wavelength band and an IR wavelength band. This series of pulses is repeated with a period of 300 ms.

In the example, there are 5 pulses, as follows:

Sync 1 (frame 1) 110 and Sync 2 (frame 2) 112: Sync pulses are used to maintain synchronisation (discussed more fully later) between the transmitter and receiver. These are pulses are preferably made in the wavelength band which is most power efficient. In this case the IR light source is used because it results in lower power consumption. Moreover the longer wavelength is more able to penetrate smoke, so synchronisation can be maintained in a greater range of conditions. The Sync pulses are 50 us long.

Ideally each synch pulses is centred in time on the leading (sync 1) and trailing edges (sync 2) of the receiver's shutter open period. This makes their received intensity vary with small synchronisation errors.

IR (frame 5) 114 and UV (frame 7) 116: The IR and UV pulses are used for signal level measurement (and in turn used to measure attenuation and smoke level.). They are 50 us long, which allows for up to 25 us timing error between transmitter and receiver without influencing the received intensity.

Data (frame 9) 118: The data pulse is used to transfer a small amount of data to the receiver. The data is encoded by a either transmitting or not transmitting the data pulse. The data pulse has reduced amplitude to save power, and is IR for the same reason. They are 50 us long. This system provides a 3 bps data channel The data may include serial number, date of manufacture, total running time, battery status and fault conditions. Those skilled in the art would be aware of many alternative ways to send data in this system. These could include pulse position encoding, pulse width encoding, and multi level encoding schemes. Greater data rates could readily be achieved, however the simple scheme used in the preferred implementation is sufficient for the small amount of data needed.

In FIG. 29, the data from the receiver during "off" frames (i.e. frames with no corresponding transmitter output) are used for the following purposes:

Frame 0 & 3 are used for background cancellation of the sync pulses

Frame 4 & 6 are used for background cancellation of the IR pulse

Frame 6 & 8 are used for background cancellation of the UV pulse

Frame 8 & 10 are used for background cancellation of the Data pulse (a) Spatial Search As described above, the receiver receives each of the transmitted pulses in the form of one or more pixels within an image frame.

However, during commissioning when the system commences operation (at least the first time) the locations of the transmitter(s) within the image frame must be established. This could be performed for example, by a manual process involving an operator inspecting the image, and programming in the co-ordinates. However, the need for special training, special tools, and long complex installation processes for installation is undesirable. In the preferred embodiment determining the location of the transmitters within the image frame is automated. The preformed process for locating transmitters operates as follows:

- The system first captures a number of images at a high frame rate and for a time sufficient to ensure that transmitter pulses, if the transmitter is within the field of view of the camera and pulses are transmitted during the period of capture, will be present in one or more images.
- The system then subtracts each pair of (temporally) adjacent images, and takes the modulus of each pixel and then tests each against a threshold to detect locations of large variation, at which a transmitter may be present.
- The system then condenses the candidate list of transmitter locations by merging candidate points that are adjacent or nearby. (e.g. <3 pixels apart) A centre of image method can be used to find the centre of a set of candidate points.
- The system then performs a trial synchronisation (using the process described below) at each of the candidate centres to verify that the received value at a candidate centre corresponds to a real transmitter.
- The system then checks that the number of transmitters matches the expected number of transmitters. This number may be set by pre-programming the receiver prior to installation, or by a switch or switches mounted on or in or connected to the receiver unit. In the preferred implementation, there is a set of configuration DIP Switches incorporated into the receiver unit and easily accessible only while the system is not mounted to the wall.

The set of transmitter locations within the image is stored in non-volatile memory. The locations can be cleared by placing the receiver into a particular mode, e.g. by setting the DIP switches to a particular setting and powering/de-powering the receiver, or by the use of a special tool, such as a notebook PC. This is only required if a transmitter is moved from its original location or the system is to be re-installed elsewhere.

Performance limitations in the imaging system may limit the number of pixels or lines that can be read out when operating at a high frame rate. In one implementation, a maximum of 30 lines of 640 pixels can be read out in 1 ms. Therefore the first few steps of the above method need to be repeated 16 times to cover the entire 640*480 image frame. Alternatively, some embodiments employ only part of the image frame. Similarly, some embodiments use a slower frame rate. However, the possibility of sensor saturation in bright lighting conditions generally limits exposure time, and variations in background lighting conditions generally introduce more noise if a lower frame rate is used.

The frame rate must be chosen to ensure that the transmitter pulses do not always occur in period where the shutter is closed. For example, if the frame rate is exactly 1000 fps, with an exposure of 100 us, and the transmitter produces pulses on exact 1 ms boundaries, the pulses may all be generated at times when the shutter is closed. The receiver frame rate is chosen so that there is a slight difference causing a gradual phase shift, ensuring that sooner or later the pulses will fall sufficiently within a shutter open period.

In some embodiments, processing speed limitations are managed by not analysing all of the pixels, instead only every fourth horizontal and vertical pixel are subtracted and checked, reducing processing effort by a factor of 16. Provided that the received image i.e. the image of each transmitter on the sensor, is spread over a sufficiently larger area (e.g. a spot having a diameter of 5 pixels), then the transmitter will still be found reliably.

Whenever the system is powered up, either with a known set of transmitter locations or as a part of the Spatial Search described above, with a set of candidate locations, a phase search and lock method is used to establish initial synchronisation.

The major steps of this method are:

The system captures images at a high frame rate (at least a partial image in the expected location).

The system waits for the expected pattern of pulse to appear at the candidate entre locations.

The system uses the time of arrival of a selected pulse within the expected pattern as a starting phase for the phase locked loop.

The system waits for stabilisation of the PLL. If no PLL lock is made, then in the case of testing candidate locations, the location is marked as spurious, otherwise when re-establishing synchronisation with a known transmitter location the receiver can re-try continually and assert a fault until it is successful.

As with the spatial search, a small offset in the receiver frame rate is used to cause a gradual phase shift, ensuring that sooner or later the pulses will fall sufficiently within a shutter open period.

For each frame, the total intensity is calculated within a small region of the image centred on the known or candidate location. This sequence of intensity values is then checked for the expected pattern from the transmitter.

The test for the expected pattern operates as follows:

After at least 9 frame intensity values have been collected, they can be tested for the presence of the expected transmitter pulse sequence in the following manner.

Given the intensity values 1(n), 0<n<N,

Test for a possible transmitter signal starting with its frame 0 at frame n received First, compute an "off frame" reference level $I_0 = (I_R(n+0) + I_R(n+3) + I_R(n+4) + I_R(n+6) + I_R(n+8))/5$ {mean of "off frames"}

Compute relative intensities $I_R(n+m) = I(n+m) - I_0$ for m=0 to 8

Compare with pre-determined thresholds to determine the presence or absence of a transmitter pulse in each frame Found = {$(I_R(n+1) > I_{ON})$ or $(I_R(n+2) > I_{ON})$} and {Sync 1 or Sync 2 pulse}

$(I_R(n+5) > I_{ON})$ and {IR pulse}

$(I_R(n+7) > I_{ON})$ and {UV pulse}

$(I_R(n+0) < I_{OFF})$ and {off frame}

$(I_R(n+3) < I_{OFF})$ and {off frame}

$(I_R(n+4) < I_{OFF})$ and {off frame}

$(I_R(n+6) < I_{OFF})$ and {off frame}

$(I_R(n+8) < I_{OFF})$ and {off frame}

Due to the random phase errors, either of the sync pulses may be completely missing, hence the "or" in the above expression. Alternatively, the tests for the sync pulses can be omitted entirely, and the tests for the off frames can also be reduced. However, care must be taken to ensure that the position of the transmitter pulse sequence is not falsely identified.

Following a positive detection, the time corresponding to the frame n is recorded in a variable. The amplitudes of the phase pulses can be used to trim the recorded time value to more closely represent the start of the sequence. This helps reduce the initial phase error that the phased locked loop has to deal with, and may not be required if frequency errors are sufficiently small.

In the preferred implementation the image capture rate 1000 fps which matches the transmitter timing as previously described. A shutter time of 100 us is used.

This completes the initial synchronisation. The arrival time of the next set of pulses can now be predicted by simply adding the known transmitter period to the time recorded in the previous step.

Although the transmitter period is known to the receiver (300 ms in the preferred implementation), there will be small errors in the clock frequencies at each end. This will inevitably cause the transmitted pulses to become misaligned with the receiver shutter open time. A Phase Locked Loop system is used to maintain the correct phase or timing. The PLL concept is well known so will not be described in detail. In the preferred implementation the PLL control equations are implemented in software. The Phase Comparator function is based on measuring the amplitude of the phase pulses. These amplitude are calculated by subtracting the mean of the intensities measured in the nearest off frames (frames 0 & 3). The phase error is then computed with the following formula:

$$\varepsilon = \frac{I_R(1) - I_R(2)}{2(I_R(1) + I_R(2))} \cdot T$$

where T is the width of the phase pulses.

In the case that the phase pulse amplitudes fall below a pre-determined threshold, the phase error is assigned a value of zero. This way noisy data is permitted into the PLL, and in practice the system is able to maintain adequate synchronisation for at least a few minutes. Therefore, high smoke levels do not cause a synchronisation failure before an alarm can be signaled. In the case of an obstruction, this feature allows the system to recover rapidly when the blockage is removed.

The PLL control equations include proportional and integral terms. It may not be necessary to use a differential term. In the preferred implementation proportional gain and integrator gains of 0.3 and 0.01 respectively were found to produce acceptable results. In a further variation, the gains can be set to larger values initially, and reduced after the phase error is below a pre-determined threshold, thus reducing overall lock time for a given loop bandwidth.

Phase error below +/−10 us can be used to indicate phase lock, both for the purpose of verifying a candidate transmitter location and also for allowing normal smoke detection operation to commence.

It will be understood that the invention disclosed and defined in this specification extends to all alternative combinations of two or more of the individual aspects or features mentioned or evident from the text or drawings. All of these different combinations constitute various alternative aspects of the invention.

It will also be understood that the term "comprises" (or its grammatical variants) as used in this specification is equivalent to the term "includes" and should not be taken as excluding the presence of other elements or features.

What is claimed is:

1. A method in a particle detector including:
a plurality of light sources; and
a light receiver, the light receiver including a light sensor, the light sensor having field of view and being capable of distinguishing light received from a plurality of regions within the field of view, and the plurality of light sources being in the field of view of the light receiver, wherein each light source is configured to emit light including a first and second wavelength into a region being monitored, the first wavelength being a wavelength whose transmission across the monitored region is relatively unaffected by particles of interest and the second being a wavelength whose transmission across the monitored region is affected by particles of interest, the method including:
receiving a plurality of light beams on the sensor, each light beam projecting across a monitored area and illuminating the light receiver whereby particles entering the monitored area cause an amount of light received by the sensor to diminish, the plurality of light beams being from the plurality of light sources, respectively;
identifying, on the basis of the output of the light receiver, at least two regions of the plurality of regions, in which light from respective light sources of the plurality of light sources is received, and
monitoring obscuration of the plurality of beams to define a plurality of beam detectors and independently determining whether particles are detected using each of the beam detectors, wherein each beam detector provides an output indicative of whether particles of interest are detected by the beam detector based on a change in the relative intensity of the light received at the first and second wavelengths.

2. The method as claimed in claim 1 which includes allocating an address on a fire alarm system corresponding to each beam detector defined by a light source in the field of view of the receiver and the receiver.

3. The method as claimed in claim 1, wherein the method includes:
approximately aligning each light source with the receiver such that the light source illuminates the receiver, and
selecting a spatial position within the field of view of the receiver corresponding to a light source to define each beam detector.

4. The method as claimed in claim 1, wherein for each beam detector, the method includes tracking a region that corresponds to its respective light source over time.

5. A particle detection system including:
a plurality of light sources adapted to illuminate a volume being monitored using a respective plurality of light beams, wherein each light source is configured to emit light including a first and second wavelength into a region being monitored, the first wavelength being a wavelength whose transmission across the monitored region is relatively unaffected by particles of interest and the second being a wavelength whose transmission across the monitored region is affected by particles of interest;
a receiver having a field of view and being adapted to receive light at the first and second wavelength from each of the plurality of sources after said light has traversed the volume being monitored wherein the plurality of light beams are received on the receiver, each light beam projecting across a monitored area and illuminating the light receiver whereby particles entering the monitored area cause an amount of light received by the sensor to diminish, the receiver being adapted to generate signals indicative of the intensity of light received at a plurality of regions within the field of view of the receiver, each light source and the receiver together defining a respective beam detector; and a processor associated with the receiver and adapted to process the signals generated by the receiver in regions within the field of view of the receiver corresponding to each light source and measure obscuration of the plurality of light beams to generate an output indicative of a particle level detected by each beam detector, wherein each beam detector provides an output indicative of whether particles of interest are detected by the beam detector based on a change in the relative intensity of the light received at the first and second wavelengths.

6. The particle detection system as claimed in claim 5, wherein the receiver includes a sensor having a plurality of sensor elements, each of which receives light from a respective region within the field of view of the receiver.

7. The particle detection system as claimed in claim 5, wherein the processor is adapted to determine a relative obscuration of light received at one or more pairs of wavelengths received from each light source and generate an output indicative of the presence of particles from each beam detector.

8. The particle detection system as claimed in claim 5, wherein the light sources are battery powered.

9. The particle detection system as claimed in claim 5, wherein the light sources are unsynchronised with each other.

10. The particle detection system as claimed in claim 5, wherein the receiver includes a camera having a sensor comprising a plurality of pixels, and where the regions of the receiver corresponding to a respective light source comprise a subset of the plurality of pixels of the sensor.

11. The method as claimed in claim 1, wherein the receiver receives light from each light source at the first and second wavelengths in the same region in the field of view.

12. The particle detection system as claimed in claim 5, wherein the receiver receives light from each light source at the first and second wavelengths in the same region in the field of view.

* * * * *

UNITED STATES PATENT AND TRADEMARK OFFICE
CERTIFICATE OF CORRECTION

PATENT NO.       : 9,645,081 B2
APPLICATION NO.  : 14/954141
DATED            : May 9, 2017
INVENTOR(S)      : Knox et al.

It is certified that error appears in the above-identified patent and that said Letters Patent is hereby corrected as shown below:

On the Title Page

In item (72), in "Inventors", in Column 1, Line 2, delete "Caufield North" and insert --Caulfield North-- therefor In item (73), in "Assignee", in Column 1, Line 1, delete "Xtralis Technologies Ltd, Nassau (BS)" and insert --Garrett Thermal Systems Ltd, Berkshire (GB)-- therefor In the Drawings On sheet 4 of 24, Fig. 4, delete "λ1, λ2" and insert --$\lambda_1$, $\lambda_2$-- therefor On sheet 6 of 24, Fig. 6, delete "λ1, λ2" and insert --$\lambda_1$, $\lambda_2$-- therefor On sheet 11 of 24, Fig. 11A, delete "λ1" and insert --$\lambda_1$-- therefor On sheet 11 of 24, Fig. 11A, delete "λ2" and insert --$\lambda_2$-- therefor On sheet 11 of 24, Fig. 11A, delete "t1" and insert --$t_1$-- therefor On sheet 11 of 24, Fig. 11B, delete "T1" and insert --$T_1$-- therefor On sheet 11 of 24, Fig. 11B, delete "λ1=λ2" and insert --$\lambda_1=\lambda_2$-- therefor On sheet 12 of 24, Fig. 12A, delete "λ1" and insert --$\lambda_1$-- therefor On sheet 12 of 24, Fig. 12A, delete "λ3" and insert --$\lambda_3$-- therefor On sheet 12 of 24, Fig. 12A, delete "λ2" and insert --$\lambda_2$-- therefor Signed and Sealed this
Twenty-ninth Day of May, 2018

Andrei Iancu
*Director of the United States Patent and Trademark Office*

On sheet 12 of 24, Fig. 12A, delete "t1" and insert --$t_1$-- therefor

On sheet 12 of 24, Fig. 12B, delete "T1" and insert --$T_1$-- therefor

On sheet 12 of 24, Fig. 12B, delete "λ1=λ3" and insert --$\lambda_1=\lambda_3$-- therefor On sheet 12 of 24, Fig. 12B, delete "t1" and insert --$t_1$-- therefor On sheet 13 of 24, Fig. 13, delete "λ1" and insert --$\lambda_1$-- therefor On sheet 13 of 24, Fig. 13, delete "λ2" and insert --$\lambda_2$-- therefor On sheet 13 of 24, Fig. 13, delete "T2" and insert --$T_2$-- therefor On sheet 13 of 24, Fig. 13, delete "t1" and insert --$t_1$-- therefor In the Specification In Column 3, Line 31, after "including:", insert --¶--

In Column 3, Line 56, delete "tem" and insert --system-- therefor

In Column 5, Line 2, delete "50% ." and insert --50%.-- therefor

In Column 7, Line 12, delete "determined" and insert --determined.-- therefor

In Column 10, Line 48, delete "FIGS." and insert --FIG.-- therefor

In Column 13, Line 7, delete "determined" and insert --determined.-- therefor

In Column 15, Line 14, delete "414." and insert --416.-- therefor

In Column 17, Line 50, after "where", insert --$\lambda_3$--

In Column 17, Line 51, after "and", insert --$\lambda_2$--

In Column 17, Line 52, after "for", insert --$\lambda_3$--

In Column 17, Line 54, before "and", insert --$\lambda_1$--

In Column 17, Line 56, delete "and," and insert --and-- therefor

In Column 17, Line 60, after "for", insert --$\lambda_3$--

In Column 18, Line 21, delete "WO02008/064396" and insert --WO2008/064396-- therefor

CERTIFICATE OF CORRECTION (continued)
U.S. Pat. No. 9,645,081 B2

In Column 22, Line 16, delete "FIG." and insert --FIGS.-- therefor

In Column 22, Line 29, delete "1304" and insert --1302-- therefor

In Column 27, Line 37, delete "322." and insert --324.-- therefor

In Column 28, Line 8, after "Texas", delete "¶"

In Column 29, Line 26, delete "100 us," and insert --100 µs,-- therefor

In Column 30, Line 47, delete "channel" and insert --channel.-- therefor

In Column 32, Line 1, delete "100 us," and insert --100 µs,-- therefor

In Column 32, Line 46, delete "1(n)," and insert --I(n),-- therefor

In Column 33, Line 15, delete "100 us" and insert --100 µs-- therefor

In Column 33, Line 58, delete "+/-10 us" and insert --+/-10 µs-- therefor